United States Patent
Wu et al.

(10) Patent No.: US 9,321,717 B2
(45) Date of Patent: Apr. 26, 2016

(54) PROCESS FOR RAPID IDENTIFICATION AND PREPARATION OF CRYSTALLINE FORMS

(71) Applicant: Allergan, Inc., Irvine, CA (US)

(72) Inventors: Ke Wu, Irvine, CA (US); Gyorgy F. Ambrus, Santa Ana, CA (US); Scott W. Smith, Mission Viejo, CA (US)

(73) Assignee: ALLERGAN, INC., Irvine, CA (US)

( * ) Notice: Subject to any disclaimer, the term of this patent is extended or adjusted under 35 U.S.C. 154(b) by 697 days.

(21) Appl. No.: 13/658,540

(22) Filed: Oct. 23, 2012

(65) Prior Publication Data

US 2013/0144077 A1 Jun. 6, 2013

Related U.S. Application Data

(60) Provisional application No. 61/550,760, filed on Oct. 24, 2011.

(51) Int. Cl.
| | |
|---|---|
| *C30B 29/56* | (2006.01) |
| *C07C 235/34* | (2006.01) |
| *C30B 7/02* | (2006.01) |
| *C30B 7/00* | (2006.01) |
| *C30B 7/08* | (2006.01) |
| *B01D 9/00* | (2006.01) |

(52) U.S. Cl.
CPC ............ *C07C 235/34* (2013.01); *B01D 9/0004* (2013.01); *B01D 9/0018* (2013.01); *B01D 9/0054* (2013.01); *B01D 9/0077* (2013.01); *C30B 7/00* (2013.01); *C30B 7/02* (2013.01); *C30B 7/08* (2013.01); *C30B 29/56* (2013.01)

(58) Field of Classification Search
CPC .............. C30B 7/02; C30B 7/08; C30B 7/00; C30B 29/54; C30B 29/56
See application file for complete search history.

(56) References Cited

FOREIGN PATENT DOCUMENTS

| WO | 2009-059605 | 5/2009 |
|---|---|---|
| WO | 2010-147625 | 12/2010 |
| WO | 2011-046915 | 4/2011 |

OTHER PUBLICATIONS

Aaltonen, Jaakko et al, Solid Form Screening—A Review, European Journal of Pharmaceutics and Biopharmaceutics, 2009, 23-37, 71.
Alleso, Morten et al, Solvent Diversity in Polymorph Screening, Journal of Pharmaceutical Sciences, 2008, 2145-2159, 97.
Alleso, Morten et al, Solvent Subset Selection for Polymorph Screening, J Chemometrics, 2008, 621-631, 22.
Bakar, Mohd Abu et al, Seeded Batch Cooling Crystallization with Temperature Cycling for the Control of Size Uniformity and Polymorphic Purity of Sulfathiazole Crystals, Organic Process Research & Development, 2009, 1343-1356, 13.
Balbach, Stefan et al, Pharmaceutical Evaluation of Early Development Candidates "The 100 mg-approach", International Journal of Pharmaceutics, 2004, 1-12, 275.
Boistelle, R. et al, Crystallization Mechanisms in Solution, Journal of Crystal Growth, 1988, 14-30, 90.
Brittain, Harry, Polymorphism in Pharmaceutical Solids, Drug and the Pharmaceutical Sciences, 1999, 4 Pages, 95.

(Continued)

*Primary Examiner* — Robert M Kunemund
(74) *Attorney, Agent, or Firm* — Jonathan Bass

(57) ABSTRACT

Disclosed is a method of rapid identification and preparation of a crystalline form of an organic compound by using sub-gram level of said organic compound, comprising the steps of temperature-cycled slurrying, cooling, antisolvent addition and solvent evaporation as the major crystallization steps.

17 Claims, 12 Drawing Sheets

(56) References Cited

OTHER PUBLICATIONS

Burger, A. et al, On the Polymorphism of Pharmaceuticals and Other Molecular Crystals. II, Mikrochimica Acta, 1979, 273-316, 2.
Byrn, S.R. et al, Solid-State Pharmaceutical Chemistry, Chemical Materials, 1994, 1148-1158, 6.
Cross, Wendy et al, A Whole Output Strategy for Polymorph Screening: Combining Crystal Structure Prediction, Graph Set Analysis, and Targeted Crystallization Experiments in the Case of Diflunisal, Crystal Growth & Growth, 2003, 151-158, 3(2).
Gardner, Colin et al, Application of High Throughput Technologies to Drug Substance and Drug Product Development, Computers and Chemical Engineering, 2004, 943-953, 28.
Gardner, Colin et al, Drugs as Materials: Valuing Physical Form in Drug Discovery, Nature, Nov. 2004, 926-934, 3.
Getsoian, A. et al, One-Solvent Polymorph Screen of Carbamazepine, International Journal of Pharmaceutics, 2008, 3-9, 348.
Gong, Yuchuan et al, Stable-Form Screening: Overcoming Trace Impurities That Inhibit Solution-Mediated Phase Transformation to the Stable Polymorph of Sulfamerazine, Journal of Pharmaceutical Sciences, Jun. 2008, 2130-2144, 97(6).
Gu, Chong-Hui et al, Grouping Solvents by Statistical Analysis of Solvent Property Parameters: Implication to Polymorph Screening, International Journal of Pharmaceutics, 2004, 117-125, 283.
Gu, Chong-Hui et al, Polymorph Screening: Influence of Solvents on the Rate of Solvent-Mediated Polymorphic Transformation, Journal of Pharmaceutical Sciences, Nov. 2001, 1878-1890, 90(11).
Gu, Chong-Hui et al, Stabilization of a Metastable Polymorph of Sulfamerazine by Structurally Related Additives, Journal of Crystal Growth, 2002, 471-481, 235.
Hassan, Mohamad et al, Characterization of Famotidine Polymorphic Forms, International Journal of Pharmaceutics, 1997, 227-232, 149.
Huang, Lian-Feng et al, Impact of Solid State Properties on Developability Assessment of Drug Candidates, Advanced Drug Delivery Reviews, 2004, 321-334, 56.
Hursthouse, Michael et al, Why Do Organic Compounds Crystallise Well or Badly or Ever so Slowly? Why Is Crystallisation Nevertheless Such a Good Purification Technique?, Organic Process Research & Development, 2009, 1231-1240, 13.
Khankari, Rajendra et al, Pharmaceutical Hydrates, Thermochimica Acta, 1995, 61-79, 248.
Kordylla, Anna et al, Modeling Ultrasound-Induced Nucleation During Cooling Crystallization, Chemical Engineering Science, 2009, 1635-1642, 64.
Lagas, M. et al, The Polymorphism of Sulphathiazole, International Journal of Pharmaceutics, 1981, 11-24, 8.
Li, Hong et al, The Application of Power Ultrasound to Reaction Crystallization, Ultrasonics Sonochemistry, 2006, 359-363, 13.
Miller, Jonathan et al, Identifying the Stable Polymorph Early in the Drug Discovery—Development Process, Pharmaceutical Development and Technology, 2005, 291-297, 10.
Mullin, J.W., Crystallization, 2001, 6 Pages, 4.
Nicolai, Beatrice et al, Polymorphism and Solvation of Indomethacin, J. Therm. Anal. Calorim, 2010, 211-216, 102.
Ostwald, W. et al, Studien uber Die Bildung and Umwandlung Fester Korper, 1897, 289-330.
Ostwald, Wilh et al, Lehrbunch Der Allgemeinen Chemie, 1896, 444.
Price, Sarah, Computed Crystal Energy Landscapes for Understanding and Predicting Organic Crystal Structures and Polymorphism, Accounts of Chemical Research, 2009, 117-126, 42.
Price, Sarah, The Computational Prediction of Pharmaceutical Crystal Structures and Polymorphism, Advanced Drug Delivery Reviews, 2004, 301-319, 56.
Pudipeddi, Madhu et al, Trends in Solubility of Polymorphs, Journal of Pharmaceutical Sciences, 2005, 929-939, 94.
Rodriguez-Spong, Barbara et al, General Principles of Pharmaceutical Solid Polymorphism: a Supramolecular Perspective, Advanced Drug Delivery Reviews, 2004, 241-274, 56.
Sato, Kiyotaka, Stability, Occurrence and Step Morphology of Polymorphs and Polytypes of Stearic Acid, Journal of Crystal Growth, 1988, 236-242, 87.
Sohn, Young et al, Study on Polymorphism of Cimetidine, J. Kor. Pharm. Sci., 1993, 81-87, 23(2).
Stahl, Heinrich et al, The Problems of Drug Interactions With Excipients, Towards Better Safety of Drugs and Pharmaceutical Products, 1980, 265-280, 39.
Threlfall, Terry, Crystallisation of Polymorphs: Thermodynamic Insight into the Role of Solvent, Organic Process Research & Development, 2000, 384-390, 4.
Tian, Fang et al, Factors Affecting Crystallization of Hydrates, Journal of Pharmacy and Pharmacology, 2010, 1534-1546, 62.
Vippagunta, Sudha et al, Crystalline Solids, Advanced Drug Delivery Reviews, 2001, 3-26, 48.
Vrecer, F. et al, Characterization of Piroxicam Crystal Modifications, International Journal of Pharmaceutics, 2003, 3-15, 256.
Patent Cooperation Treaty, Notification of Transmittal of the International Search Report and the Written Opinion of the International Searching Authority, or the Declaration, Form PCT/ISA/220, Int. App. No. PCT/US2012/061491, Feb. 27, 2013.
Alvarez, A., et al., Polymorph Screening: Comparing a Semi-Automated Approach with a High Throughput Method, Crystal Growth and Design 2009, 9: 4181-4188.
Morisette, Sherry L., et al., High-throughput crystallization: polymorphs, salts, co-crystals and solvates of pharmaceutical solids, Advanced Drug Delivery Reviews 2004, 56: 275-300.

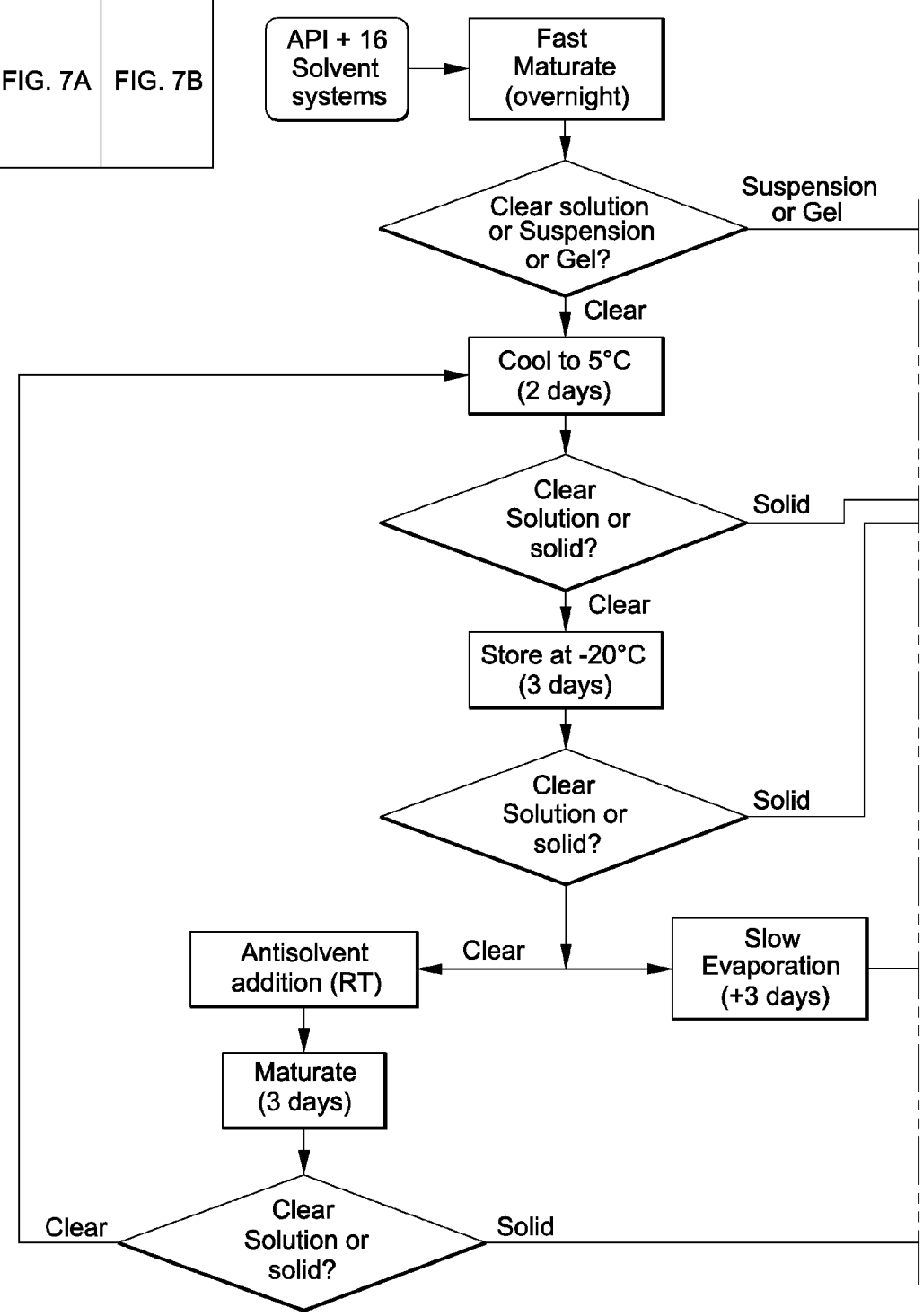

PROCESS FOR RAPID IDENTIFICATION AND PREPARATION OF CRYSTALLINE FORMS

CROSS REFERENCE TO RELATED APPLICATIONS

This patent application claims the benefit of U.S. Provisional Patent Application No. 61/550,760, filed on Oct. 24, 2011, which is hereby incorporated by reference in its entirety.

FIELD OF THE INVENTION

Disclosed herein is a method of rapid identification and preparation of a crystalline form of an organic compound by using sub-gram level of said organic compound, comprising the steps of temperature-cycled slurrying, cooling, antisolvent addition and solvent evaporation as the major crystallization steps.

BACKGROUND OF THE ART

The physical form of an active pharmaceutical ingredient (API) has great significance from the perspectives of drug product performance, intellectual property protection, and regulatory compliance, etc.[1-3] The quality of the lead candidates can be favorably impacted by early consideration of "developability" criteria along with efficacy and safety studies.[4,5] For instance, if non-developable forms, such as oils, amorphous materials, and some solvates, etc., were elevated, lots of downstream development difficulties would emerge. These difficulties could severely delay the formulation development process as well as other project-relevant activities. In addition, on the discovery side, efficacy and safety studies might not be conducted because of the challenges caused by those form issues.

Currently various API-sparing experimental strategies are proposed and practiced to rapidly and effectively evaluate the polymorphism and crystallization tendency of the compounds advancing from discovery into early development Although both experimental and theoretical strategies have been focused in the area of crystallization and polymorphism,[1,7-10]; however there are severe limitations associated with the existing methods:

First of all, computational methods are far from practical application because they are very expensive, time-consuming, and specially-trained talents are required. More importantly, the predictive power on polymorphism is not satisfying so far.[11]

As for experimental methods, high-throughput form screening is not quite satisfying, which is often attributed to the consensus that polymorph screening is partially both science and art. In fact, the fundamental reason is lack of fundamental understanding of polymorphism. In addition, more comprehensive polymorph screening on discovery compounds before elevation is not realistic because of its cost- and time-ineffectiveness at this stage.

Therefore, a process for risk assessment of discovery compounds is needed before their elevation for development, as this would greatly facilitate the identification of those drug candidates with the most promising developability. The present invention provides such a process.

Sherry L. Morissette et al., *Advanced Drug Delivery Reviews* 56 (2004) 275-300, reviews and highlights the opportunities and challenges of high throughput crystallization technologies as they apply to pharmaceutical research and development.

Alejandro J. Alvarez et al., *Crystal Growth and Design*, 2009, Vol. 9, No. 9, 4181-4188, compares the polymorph screening studies of various compounds using a semi-automated apparatus with a high-throughput method.

BRIEF SUMMARY OF THE INVENTION

The present invention provides a process for the rapid identification and preparation of a crystalline form of an organic compound by using sub-gram level of said organic compound, said process comprising the steps of temperature-cycled slurrying, cooling, antisolvent addition and solvent evaporation as the major crystallization steps.

In one embodiment, the above process comprises the steps of:

(a) Conducting an initial x-ray powder diffraction (XRPD) analysis of a starting sample of said organic compound; thereafter (b) Conducting an initial visual solubility estimation of the organic compound in each of several solvents or a mixture of solvents thereof at ambient or room temperature; thereafter (c) Conducting a solubility estimation of the organic compound in each of a subset of the several solvents of step (b) or a mixture of said solvents at elevated temperature by subjecting a suspension or emulsion of the organic compound in said solvent or solvent mixture to temperature-cycled slurrying for a fixed period of time; and thereafter performing any one of: i) steps (d1) through (d5), (e1), (e2) and (f4); ii) steps (f1) through (f4); iii) steps (d1), (e1), (e2) and (f4); iv) steps (d1), (d2), (e1), (e2) and (f4); and (v) steps (d1) through (d4), (e1), (e2) and (f4) set forth below:

(d1) If the sample of the organic compound and solvent/solvent mixture from step (c) remains a clear solution, then cooling the solution of said organic compound in said solvent or solvent mixture to a temperature of about 3° C. to about 6° C. and maintaining said solution at said temperature for a fixed period of time to induce super saturation;

(d2) If the sample of the organic compound and the solvent/solvent mixture is still a clear solution at the end of said fixed period of time in step (d1), then further cooling said solution to a temperature of about −18 to about −22° C. for a fixed period of time that is longer than the period of time set forth in step (d1) above;

(d3) If the sample of the organic compound and the solvent/solvent mixture is still a clear solution at the end of said fixed period of time in step (d2), then adding an antisolvent/antisolvent mixture at room temperature to create a suspension or emulsion of the organic compound in said mixture of solvent and antisolvent;

(d4) Further subjecting said suspension or emulsion of the organic compound in said mixture of solvent and antisolvent from step (d3) to temperature-cycled slurrying for a period of time longer than that set forth in step (d1);

(d5) If the sample of the organic compound and the mixture of solvent and antisolvent at the end of step (d4) is a clear solution, then further performing steps (d1) through (d4) once more as long as the sample of the organic compound and the solvent/solvent mixture in steps (d1) and (d2) is still a clear solution;

(e1) If the sample of the organic compound and the solvent/solvent mixture at the end of any of steps (d1) or (d2) are not clear solutions, or the sample of the organic compound and the mixture of solvent and antisolvent at the end of step (d4) is not a clear solution, then performing a filtration to isolate a "dry" sample of said organic compound from the solvent/solvent mixture or solvent/antisolvent mixture;

(e2) evaporating the solvent/solvent mixture or the solvent/antisolvent mixture from step (e1) in a slow, diffusion controlled process for a fixed period of time that is at least 24 hours long to isolate the residue, which is a "wet" sample of the organic compound;

(f1) further subjecting the sample of the organic compound and the solvent/solvent mixture to temperature-cycled slurrying for a period of time longer than that in step (c) if said sample of the organic compound and the solvent/solvent mixture is not a clear solution;

(f2) performing a filtration to isolate a "dry" sample said organic compound from the solvent/solvent mixture in step (f1);

(f3) evaporating the solvent/solvent mixture from step (f2) in a slow diffusion controlled process for a fixed period of time that is at least 24 hours long to isolate the residue which is a "wet" sample of the organic compound;

(f4) conducting an XRPD analysis of wet and dry samples of said organic compound from any of step (e1), (e2), (f2) and (f3) and compare said analysis with the analysis carried out in step (a);

wherein significant differences in the XRPD spectra between the sample in step (a) and the sample in any one of steps (e1), (e2), (f2) and (f3) likely indicate the presence of a new crystalline form of said organic compound.

In another embodiment of the present invention, the organic compound is an active pharmaceutical ingredient (API).

In another embodiment of the present invention, the sub-gram level of said organic compound is an amount that is less than 350 mg.

In another embodiment of the present invention, step (b) comprises estimating the solubilities of the organic compound in at least 20 different solvents.

In another embodiment of the present invention, the starting sample in step (a) is an amorphous or crystalline material.

In another embodiment of the present invention, in step (c), the temperature-cycled slurrying is conducted with a single solvent, and wherein the concentration of said suspension or emulsion of the organic compound in the single solvent at ambient or room temperature is 5-10 times lower than the concentration at elevated temperature.

In another embodiment of the present invention, in step (c), the fixed period of time is about 20 to about 26 hours.

In another embodiment of the present invention, in step (c), the temperature-cycled slurrying involves at least three heat-cool-heat temperature cycles.

In another embodiment of the present invention, in step (d1), the cooling is carried out at a cooling rate of about 0.1° C. per minute.

In another embodiment of the present invention, in step (d2), the cooling is carried out at a cooling rate of about 0.1° C. per minute.

In another embodiment of the present invention, in step (d1), the fixed period of time is about 22 to about 26 hours.

In another embodiment of the present invention, in step (d2), the fixed period of time is about 2 to about 6 days.

In another embodiment of the present invention, in step (d4), the fixed period of time is about 2 to about 7 days.

In another embodiment of the present invention, in steps (e2) and (e3), the fixed period of time is about 2 to about 6 days.

In another embodiment of the present invention, the crystalline form being prepared is the most thermodynamically stable crystalline form.

In another embodiment of the present invention, the present inventive process has the advantage of in being completed in a period of about 2 to about 3 weeks.

In another embodiment of the present invention, the present process has the advantage of facilitating decision-making on the developability of a drug candidate.

In another embodiment of the present invention, the organic compound is an active pharmaceutical ingredient (API), and wherein the present process has the advantage of enabling an organic compound drug candidate to be elevated to early development.

BRIEF DESCRIPTION OF THE DRAWING

FIGS. 7A and 7B shows the FRA experimental Workflow for Compound H.

DETAILED DESCRIPTION OF THE INVENTION

The present invention provides a process for the rapid identification and preparation of a crystalline form of an organic compound by using sub-gram level of said organic compound, said process comprising the steps of temperature-cycled slurrying, cooling, antisolvent addition and solvent evaporation as the major crystallization steps.

In the drug development field, this process is therefore a stage-appropriate form risk assessment (FRA) of discovery compounds before their elevation for development may greatly facilitate the identification of those drug candidates with the most promising developability. This resource-saving strategy can and does provide long-term effectiveness in drug development.

The present process allows one to develop and evaluate a medium-throughput process that rapidly crystallizes and potentially identifies polymorphs and/or pseudo-morphs by using sub-gram level of API. This process presents a workflow that can (1) evaluate the risks associated with the solid-state forms of discovery compounds using a low- to medium-throughput screening methodology and (2) give recommendation on a low risk form for further development within a few weeks. Such a procedure, if performed early in the development process, may be able to mitigate the downstream risks associated with physical form changes, and to help differentiate the drug candidates based on their propensities to form multiple crystalline forms.

Figure 1:
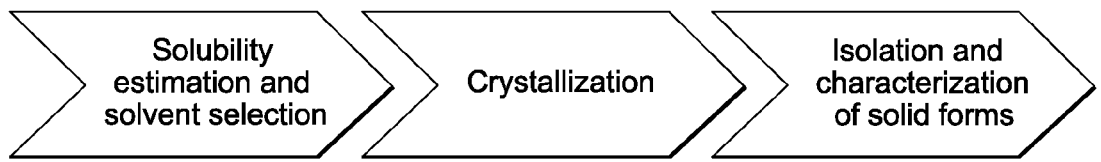
FIG. 1 shows the general scheme of the FRA workflow.

FIG. 1 presents the general scheme of the FRA workflow.

In the solubility estimation and solvent selection stage, the experiment focuses on choosing suitable solvents and designing proper solvent mixtures to maximize the "hit" rate of crystallization. In the crystallization stage, the workflow features a well-controlled temperature-cycled slurrying experiment with the aim of increasing the quality of the final products in terms of polymorphic purity and crystallinity. In the final stage, the solid forms are characterized by suitable techniques to help deciding further steps. A detailed description on the FRA workflow is discussed in Section 1.2.1.

| Abbreviations used in this document | |
|---|---|
| API | Active pharmaceutical ingredient |
| CRO | Contract research organization |
| FRA | Form risk assessment |
| XRPD | X-ray powder diffractometry |
| DSC | Differential scanning calorimetry |
| TGA | Thermogravimetric analysis |
| NMR | Nuclear magnetic resonance spectroscopy |
| HPLC | High performance liquid chromatography |
| DS | Drug substance |
| FTIR | Fourier transform infrared spectroscopy |
| VSA | Vapor Sorption Analysis |
| RT | Room Temperature |

1. MATERIALS AND METHODS

1.1 Materials

1.1.1 Model Compounds

A number of compounds with published properties and polymorphic forms[11-19] were selected as model compounds to develop and verify the FRA workflow. All drug substances were purchased from Sigma-Aldrich without further purification. Detailed information on these properties can be found in Appendix I.

Table 1 summarizes the Allergan compounds studied by applying the FRA workflow.

TABLE 1

Allergan Compounds Studied in FRA.

| # | Compound | Project/Program | Project/Program Stage | Initial Solid Form |
|---|---|---|---|---|
| 1 | Compound A | MKI | Gate 1 | Amorphous |
| 2 | Compound B | Bimatoprost IC | Gate 2-3 | Amorphous/ non-solvated |
| 3 | Compound C | Keto IC | Full development | Amorphous/ non-solvated |
| 4 | Compound D | MKI | Pre-Gate 1 | Amorphous |
| 5 | Compound E | MKI | Pre-Gate 1 | Crystalline |
| 6 | Compound F | Fatty Acid | Pre-Gate 1 | Crystalline/ non-solvated |
| 7 | Compound G | Fatty Acid | Pre-Gate 1 | Crystalline/ non-solvated |
| 8 | Compound H | CsA Analog | Gate 2-3 | Amorphous |
| 9 | Compound I | MKI | Pre-Gate 1 | Amorphous |
| 10 | Compound J | Rosacea | Gate 1-2 | Crystalline/ Hydrate |

These compounds were at different development stages and were evaluated by FRA on a fit-for-purpose basis. In some cases, amorphous compounds needed to be crystallized; in others, the polymorphic tendencies of compounds needed to be preliminarily assessed.

1.2 Methods 1.2.1 Strategic FRA Workflow Because each compound has a unique structure and, hence, different properties, it is not possible to establish a universal FRA protocol. However, certain basic elements of the polymorph screening experiments are incorporated, such as solubility estimation, solvent-mediated form transformation, as well as super saturation adjustment by cooling, antisolvent addition, and evaporation, etc. The following procedure outlines the logical steps of performing an FRA experiment:

1. Determine the physicochemical properties of the starting material (compound as received)
2. Estimate the solubilities of the compound in twenty-four solvents with diverse solvent properties.
3. Design approximately sixteen crystallization experiments with appropriate solvent systems based on the results of the solubility estimations.
4. Prepare the crystallization samples and examine their solubilities in the sixteen solvent systems at elevated temperature.
5. Conduct the crystallization experiment according to the designed workflow.
6. Characterize and analyze the materials isolated from the crystallization experiments.

Figure 2:
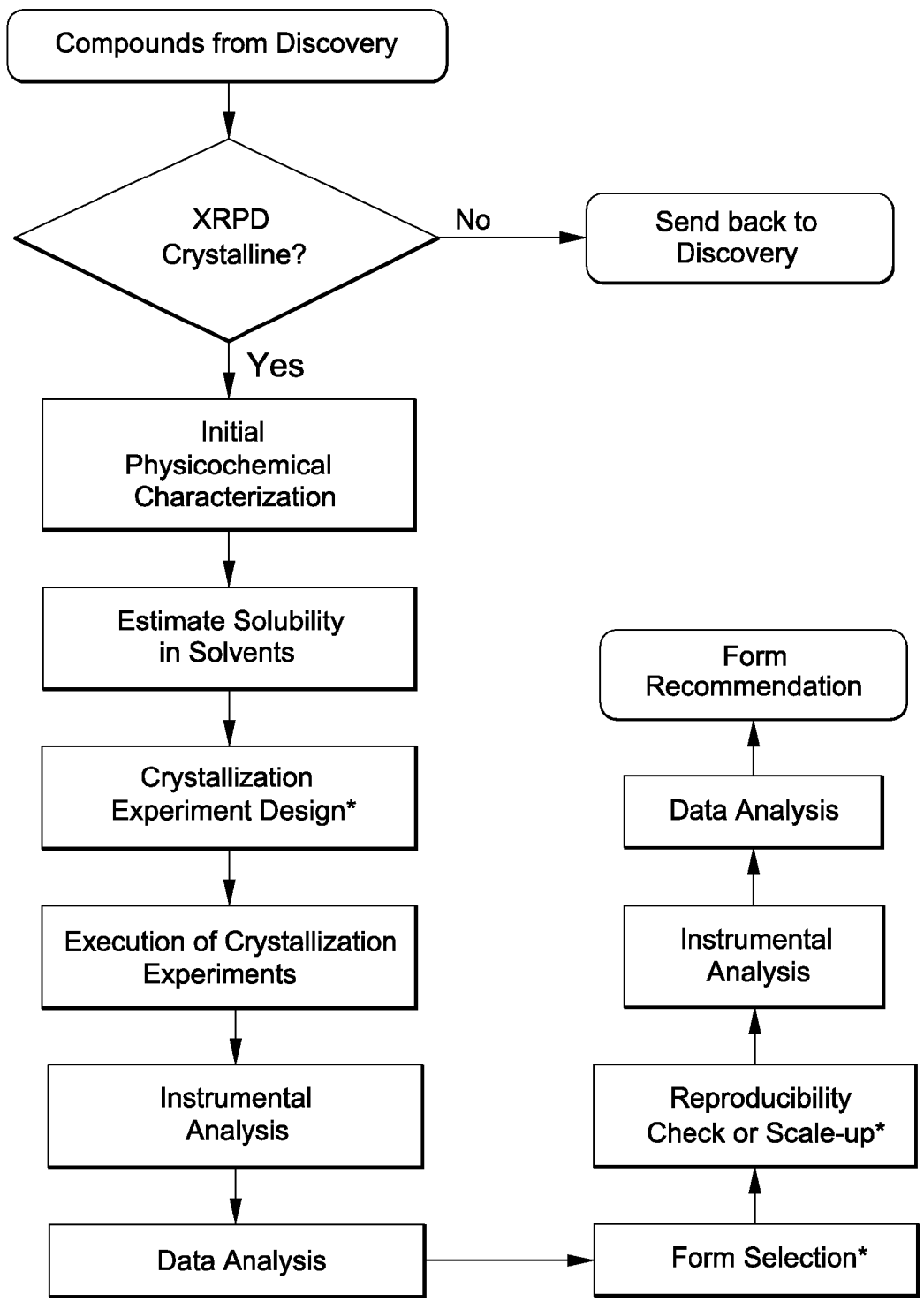
FIG. 2 shows the FRA workflow diagram at Allergan Physical Chemistry.

A general FRA workflow is shown in the flowchart shown herein as FIG. 2.

From the preliminary physicochemical characterization, an initial profile of the drug substance candidate emerges and is used as a reference for future data analyses. This work can be integrated with the preparation of the physicochemical data package for elevation assessment. The solubility of the FRA compound in a variety of solvents is estimated to facilitate the selection of the crystallization technique and the experimental sequence. Finally, the following scale-up studies should be conducted as appropriate:

1. Scale up (20-30 mg) the experiments which generate materials of interest.
2. Build stage-appropriate physicochemical profiles of the materials.
3. Conduct bridging studies to understand the thermodynamic relationships of different forms if applicable.

More details on the key steps are discussed in Section 2.2.5.

1.2.2 Characterization of Drug Substance Candidates

The compounds received from medicinal chemists are initially screened with XPRD to check whether the material is crystalline or amorphous. The compound will also be analyzed by DSC and TGA to detect the existence of hydrates or solvates. If necessary, the add-on Mass Spec. module to the TGA system can be used to determine the nature of the solvent. Table 2 summarizes the initial characterizations for the as-received discovery compounds.

TABLE 2

Summary of the Initial Evaluations on the FRA Candidates.

| Properties of the compound as received | Description | Experimental Method |
|---|---|---|
| Physical state | oil or solid | Visual Inspection |
| Physical form | crystalline or amorphous | XRPD |
| Hydration (Solvation) state | anhydrous, desolvated, solvate, hydrate, etc. | TGA |
| Thermal properties | melting temperature, glass transition temperature, decomposition temperature, etc. | DSC |

More importantly, timely communication with medicinal chemistry and process chemistry often provides valuable information for the understanding of the as-received material. Table 1 in Appendix 1 describes the characterization experiments and the amount of material needed for each experiment.

1.2.3 Initial Treatment of the Starting Material

Ideally, amorphous materials should be prepared and used for polymorph screening, because ideally the crystalline history should to be erased to avoid the seeding effect. However, anhydrous or de-solvated crystalline material is also acceptable for FRA because the current study is aimed at identifying the low-energy form instead of trying exhaustive form screening.

When the starting material is determined to be a hydrate or a solvate, the guest molecule(s) should be removed, if possible, by reasonable efforts, e.g., heating or vacuum. If still present, the water or organic solvent molecule might interfere with the crystallization experiments, potentially causing biased results towards certain hydrates or solvates.

1.2.4 Solubility Estimation in Various Solvents

Knowledge of the solubility of the drug substance in different solvents is vital for the success of any crystallization and polymorph screening effort.[20] The current strategy is to build a design space covering sufficient solvent property ranges and then to estimate the solubility. This design space was constructed based on the information from external reports, literatures, and regulatory guidelines.

1.2.4.1 Initial Solubility Estimation

The solubility of the API is visually estimated by the "dynamic method" in each of the twenty-four solvents. This method is used to quickly bin the solvents into different categories, such as good solvents, poor solvents, and intermediates. The following describes the general procedure of the solubility estimation:

1. Place weighed amounts of drug in clear glass vials to which incremental volumes (20-500 µL) of solvent are added until the solution turns clear.
2. Apply brief vortexing after each solvent addition.
3. Calculate the approximate visual solubility of the drug in a solvent by recording the amount of solvent required to completely dissolve the known weight of drug. The preferred unit of solubility is mg/mL.

The concentration where the compound completely dissolves is considered as the approximate solubility of the compound in a specific solvent at that temperature, usually ambient (22±2° C.). The apparent solubility is expressed as "less than" if dissolution does not occur during the experiment. If complete dissolution is achieved as a result of only one aliquot addition, the solubility is expressed as "greater than." Otherwise, a solubility range is used.

The solute-solvent affinity, as expressed by the solubility value, will be used for deciding the composition of the crystallization samples. Although different criteria were reported for isothermal slurrying experiments,[23] the following are generally recommended to classify the solvents:

When solubility is less than 1 mg/mL, the solvent can be used as antisolvent or solvent for thermo-cycled slurrying experiment.

When solubility is between 1-100 mg/mL, the solvent can be used as solvent for thermo-cycled slurrying experiment.

When solubility is greater than 100 mg/mL, the solvent can be used as solvent to mix with antisolvent for slurrying experiment.

The above solubility value thresholds are the result of experimental estimation,[5] therefore they may be modified for designing FRA experiments on a case-by-case basis.

1.2.4.2 Solubility Estimation at Elevated Temperature

The suspensions of the drug substance in a variety of solvent systems will be subjected to temperature-cycled slurrying, which is the primary crystallization method. Sixteen sample slurries for thermo-cycled experiments should be prepared with caution to avoid complete dissolution of the solid at elevated temperatures. For slurry with a single solvent system, the initial composition should have approximately 5-10 times higher concentration than the estimated solubility value at ambient temperature. For slurry in a solvent mixture, a suspension of the compound in the antisolvent should first be prepared and followed by the introduction of the solvent to adjust the solubility. The final antisolvent to solvent volume ratio is typically between 3 and 10. Record the amount of compound initially added and the volumes of added solvent aliquots.

Once the composition is finalized, the clarity of the suspension should be inspected at 45° C. Additional antisolvent should be introduced if all solid dissolves upon heating; otherwise, a thermo-cycled slurry experiment can be initiated with the same suspension.

1.2.5 Crystallization Methods

Four major crystallization techniques are adopted in this workflow: thermo-cycled slurrying, cooling, antisolvent addition, and solvent evaporation. Numerous literature articles have discussed the latter three methods.[24,25] The focus of this FRA workflow is thermal-cycled slurrying because it can potentially accelerate the form screening with the possibility of obtaining the more stable form under the experimental conditions studied.

1.2.5.1 Thermocycling

Theoretically, an isothermal slurrying experiment favors the formation of the more stable form. However, the kinetics of the form conversion or crystallization is highly solubility-dependent. A solvent-mediated form transformation may take a long period of time if the solubility of the material is limited in the solvent or the solubility of the forms is very similar in the same solvent. Thermocyled slurrying utilizes temperature fluctuations to increase the kinetics of Ostwald ripening[26] as well as polymorphic conversion. During the thermocycled process, the dissolution of fine particles (and/or metastable polymorphic forms) is accelerated during heating ramps, while the growth of the larger crystals or more stable form is accelerated during cooling ramps. As a result, polymorphic purity of drug crystals can be improved by exerting the temperature cycling.[27]

Appendix 1 summarizes the typical temperature programs for each experiment. Usually three heat-cool-heat temperature cycles are used. The initial fast thermocycling runs help preliminarily assessing the dissolution behavior of the samples. The slow thermocycling runs focus on generating crystals and increasing the crystallinity and form purity.

1.2.5.2 Cooling Experiments

If the sample remains a clear solution after the initial thermocycling, the solution is cooled to induce super saturation. During cooling, the original solution may become supersaturated and further reach the metastable limit when spontaneous crystallization starts. Usually the final temperature is 5° C. and the cooling rate is 0.1° C. per minute to facilitate crystal growth.

If the sample is still a clear solution at 5° C., the sample vial will be transferred into a −20° C. freezer for at least 2-3 days. The sample should be regularly examined by visual inspection and/or polarized light microscope for signs of solid formation.

1.2.5.3 Antisolvent Addition

The antisolvents identified during the initial solubility estimation can be used for adjusting the solubility of the drug substance in the primary solvent. The combination of a solvent with a miscible antisolvent provides a continuous solvent space, which potentially maximizes the possibility of capturing a crystalline form. The miscibility between the antisolvent and solvent within the experimental composition is recommended for effective solubility modification. However, the solubility of the drug substance in a binary solvent mixture does not necessarily follow a simple linear relationship with the composition of the mixture; the temperature dependence of the solubility is also unpredictable. Preferably, the antisolvent rather than the solvent should be introduced first. If the sample preparation starts with an antisolvent, it is more feasible to create a suspension, adjust the cloudiness by adding some solvent, and then re-adjust the sample to cloudy suspension with an additional small volume of antisolvent. As a result, maintaining the sample as a suspension or emulsion at elevated temperatures is more achievable.

1.2.5.4 Solvent Evaporation

Evaporation is used for the isolation of the drug substance from a clear solution. This technique is used when the solids cannot be isolated by filtration. When the solvent systems contain low-vapor-pressure solvents, the following can be used to accelerate the evaporation: (1) nitrogen purging, (2) heating, (3) vacuum, and their combination. Furthermore, the evaporation of the solvent during thermocycling is also optional when there is no sign of solid formation after the initial thermal cycles. In this case, a syringe needle is inserted through the septum of the cap of the crystallization vial with the tip of the needle slightly above the liquid surface for diffusion controlled slow evaporation.

2. RESULTS AND DISCUSSION

2.1.1 Solvent Design Space

The general consensus on crystallization solvents is to include a collection of solvents with as diverse properties as possible. However, the number of solvent candidates for FRA is limited to twenty-four because of resource limitations. The following describes the rationale for the FRA solvent selection:

1. Several solvents from each group were first selected as the initial candidates by adopting the published criteria.[20,21]
2. The solvents within each group were rank ordered according to their tendency to solvate formation as confirmed by the CCDC database. The ones with greater frequency were assigned more weight in the ranking.
3. The solvents that are commonly used for manufacturing were given preference over those that are less frequently or never used.
4. The solvents with the least regulatory concerns according to the ICH solvent classification guidance, were deemed more desirable.
5. The solvents potentially causing chemical stability issues were eliminated.
6. The considered properties and reasons, as outlined above were used to generate a list of twenty-four solvents.

Figure 3:
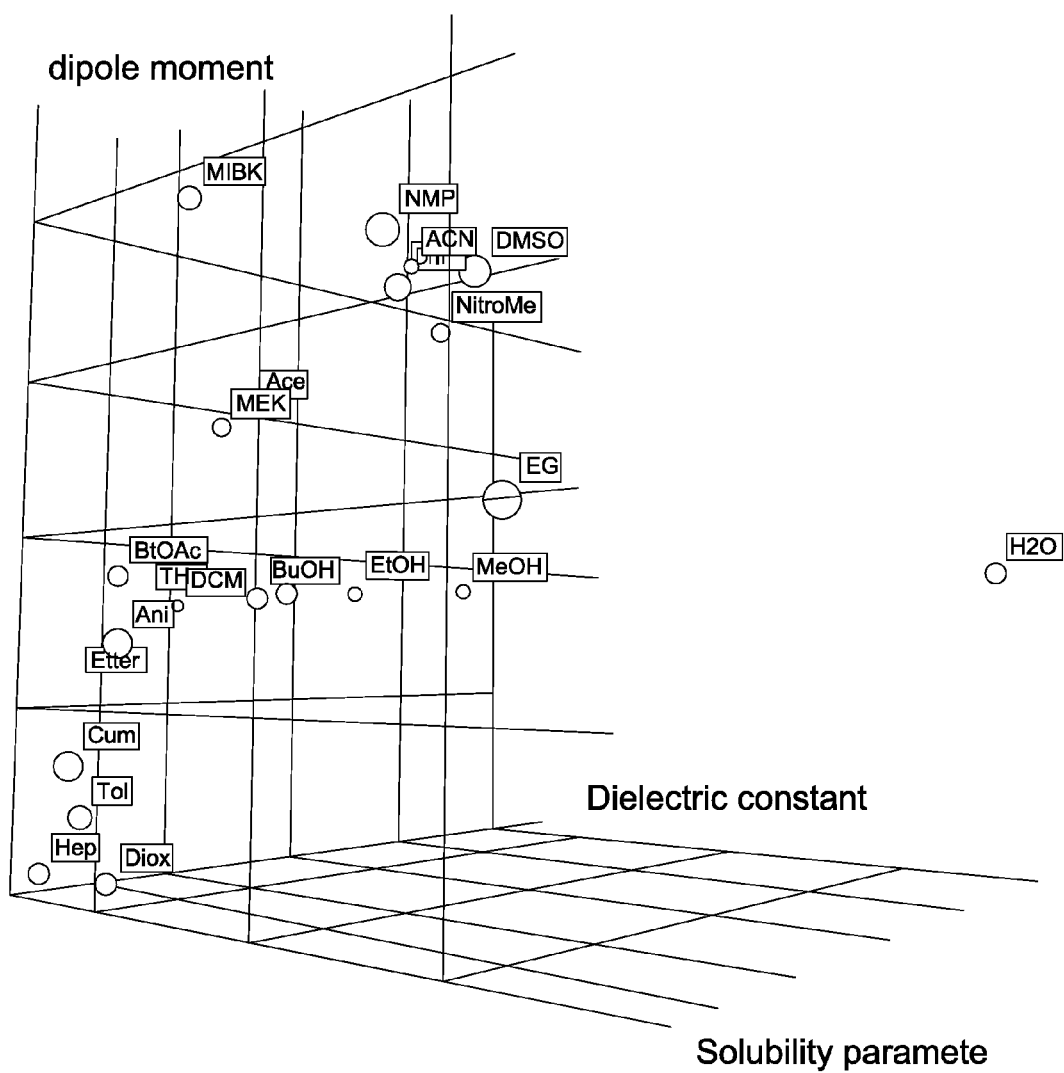
FIG. 3 shows The Solvent Property Space Created for FRA.

When a crystallization process is under thermodynamic control, then the nature of the solvent will have no relationship with the polymorph formed.[28] Although solvents can be either critical or immaterial in the formation of specific polymorphs,[29] the crystallization of a molecule is frequently under kinetic control. Generally, molecules in solution often tend to form various types of specific interactions, such as hydrogen-bonding, with different solvent systems. These interactions may facilitate the formation of certain molecular aggregates, serving as precursors for the crystal structures built in the supersaturated solution.[39] In addition, the degree of super saturation can also affect the type of crystals formed, which can be manipulated by using solvents with different solubility parameters. Therefore, we use three properties of the solvents, namely, dipole moment, dielectric constant, and solubility parameters, to reflect the solvation power, solute-solvent affinity, and specific interaction of the solvents. These properties were considered to be affecting the crystallization process more or less directly. The solvent property space built in this work is illustrated in FIG. 3. Specifically, up to sixteen crystallization solvent systems were selected from twenty-four candidate solvents to represent wide ranges of solvent properties: dipole moments between 0-4.2 debye, dielectric constants between 1.9-80.4 and solubility parameters between 14.1-45.8 $(MPa)^{1/2}$.

In addition, among all the solvents of pharmaceutical relevance, the water molecule is found to be more capable of linking to drug molecules to form new crystal structures than any other solvent. Crystalline hydrate formation has been observed with about one-third of drug substances,[31] largely because the water molecule is small, active, and able to act as both a hydrogen bond donor and acceptor. More importantly, interactions between drug molecules and water molecules are frequently encountered during processing, formulation, and drug delivery. Therefore, water as a solvent or antisolvent should always be considered when designing the form risk assessment experiments unless it causes chemical stability issues.

2.2 Model Compound Design Space

Three properties of each model compound are used for building the model compound space: intrinsic solubility ($S_0$), partition coefficient (log P), and melting temperature. Although these properties have not been used to directly predict the polymorphic propensity of a material at the molecular level, they are legitimate indicators of the cohesive energy and the tendency of potential intermolecular interactions such as hydrogen bonding.

Figure 4:
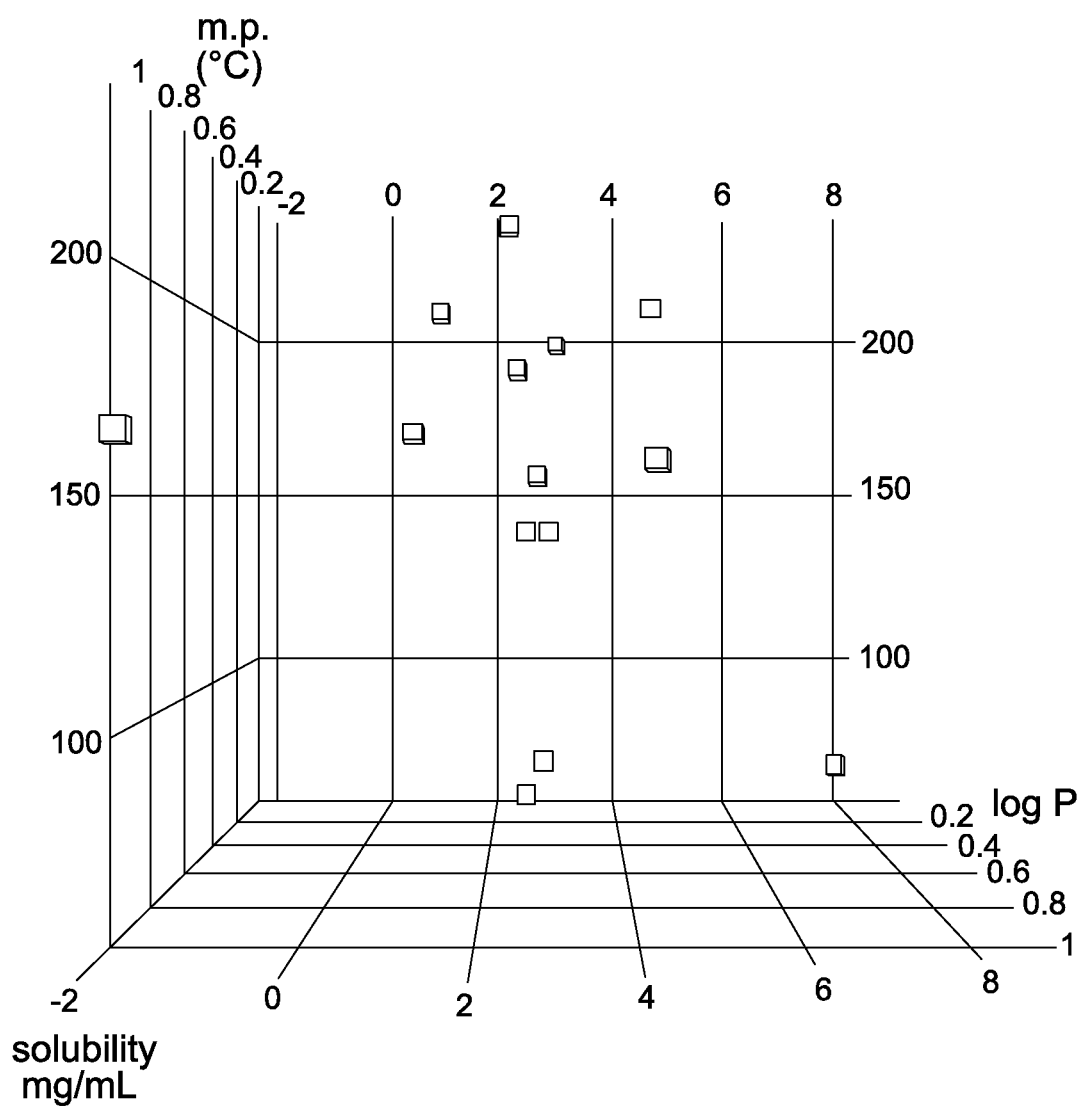
FIG. 4 shows Model Compound Design Space for FRA.

The design space is presented in FIG. 4. The studied model compounds cover a design space with the following parameters:
  intrinsic solubility (0.0006-1.1 mg/mL),
  melting point (68-210° C.),
  Octanol/water partition coefficient (log P between −2.1 and 8.0).

This design space is considered to be able to generally cover the common compounds coming from the discovery groups.

2.3 Form Risk Assessment on Model Compounds

Table 3 compares the experimental results of the FRA conducted on nine model compounds by Allergan Physical Chemistry with those reported in the literature. All the model compounds were crystalline and used as received. Regardless of the initial form of the starting material, the FRA workflow was able to capture the low energy forms for all of the compounds. This is indicated by an "*" next to the form label designation.

TABLE 3

Summary of Results on FRA of Model Compounds.

| Model Compounds | Reported Forms in the Literature | Forms Found by FRA | FRA_TC | FRA_AS | FRA_5° C. | FRA_20° C. | FRA_EV |
|---|---|---|---|---|---|---|---|
| Piroxicam | I*, II, III, hydrate | I*, II, hydrate | I, II, hydrate | | | | I, II |
| Ketorolac free acid | I*, II, III, solvate | I*, solvate | I | I, solvate | | I | |
| Indomethacin | α, β, γ* | α, β, γ* | α, β, γ | | | | |
| Carbamazepine (E) | α*, β*, γ, dihydrate, solvate | α*, β*, γ | α, β, γ | | | | γ |
| Mebendazole | A*, B, C | A*, B, C | A, B, C | | | | |
| Famotidine | A*, B | A*, B, C (new form) | A, C | A | C | | A, C |
| Stearic acid (E) | A, B*, C*, E | B*, C* | B, C | | | | |
| Sulfathiazole | I, II, III*, IV*, V | I, II, III*, IV* | I, II, III, IV | | | | |
| Diflunisal | I*, II, III, IV, 2 solvates | I*, II, III, IV, 1 solvate | I, II, III, IV | | IV | | I, IV, solvate |

Note:
TC: thermocycled slurrying; AS: antisolvent; 5° C.: cooling to 5° C.; EV: evaporation.

Within the design space defined by the model compounds, the thermocycling method in the FRA workflow identified the low-energy forms, as shown in Table 3. These results suggest that the thermocycling method may accelerate the formation of the most stable form.

Most but not all of the metastable forms of the model compounds were found. The discovery of metastable forms can be used for candidate selection or designing further polymorph screening studies. According to Ostwald, "when leaving a metastable state, a given chemical system does not seek out the most stable state, rather the nearest metastable one that can be reached without loss of free energy".[32,33] Although this is usually the rule, exceptions were not sparse because of various confounding factors such as solvent-solute interactions, thermodynamics, as well as the kinetics of nucleation, growth and transformation, etc. This could explain the observation that multiple forms were often identified in the FRA experiments.

It is worth noting that the FRA in essence is not a comprehensive polymorph screening but rather an abbreviated crystallization process. Therefore, the polymorphism reported in the literature was not exhaustively captured herein. For example, the dihydrate of carbamazepine was not captured by the FRA, reflecting the limitation of the workflow, i.e., the design of the crystallization experiments are primarily based on the results of solubility estimation. Many drug substances have limited solubility in water, leaving water as a common antisolvent for crystallization experiments. Even though water activity is one of the key parameters affecting the formation of hydrates, the FRA flow usually does not cover a spectrum of water activities because the focus is not solely on hydrate screening. As a result, the hydrate formation might not be specifically covered by the FRA workflow and hence it deserves a separate well-designed experimental strategy.

Next, both enantiotropic polymorphs of carbamazepine and stearic acid were formed by the FRA experiments, indicating that the enantiotropism of a compound can be possibly identified by using diverse solvent systems. Enantiotropism refers to a thermodynamic relationship between two polymorphs where one form is more stable over a certain temperature range and pressure but another one is stable over a different range. Two polymorphs of the same substance have a monotropic relationship when one of them is more stable than the other regardless of the temperature (below melting). It is worth noting that the thermocycling experiments could introduce additional variable when the transition temperature for an enantiotropic system is bracketed by the temperature limits. Therefore, the enantiotropism of a compound may not be sufficiently captured by the FRA and hence it should be investigated further.

Finally, the published polymorph screening methods used for the model compounds were different with respect to crystallization strategies; however, they are not applicable for supporting early development because of their time- and API-consuming nature. In contrast, the FRA approach obtained comparable results to those of the published studies, but were performed within the targeted API and time constraints.

2.4 Form Risk Assessment on Proprietary Compounds

Table 4 summarizes the results of the FRA studies on a number of Allergan compounds.

TABLE 4

Summary of the Results on FRA of Allergan Compounds

| Compound | Project/Program | Starting Form | Forms found by FRA | Outcome |
|---|---|---|---|---|
| Compound A | TKI | Amorphous | Pattern 18* (Solvate of the most stable form) | First FRA test run |
| Compound B | Bimatoprost IC | Form 1 | Forms 1, 2, and 3 F2: low energy form at higher Temp. | Filed Record of Invention on new forms |
| Compound C | MKI | Amorphous | Forms 1 and 2 | Crystalline forms supported Medchem group meet early lead criteria |

TABLE 4-continued

Summary of the Results on FRA of Allergan Compounds

| Compound | Project/Program | Starting Form | Forms found by FRA | Outcome |
|---|---|---|---|---|
| Compound D | MKI | Amorphous | Forms 1, 2, and 3 | Became Back up of Compound C |
| Compound E | Pan PG antagonist | Form 1 | Form 1 | Support CMC project progressing, New Record of Invention filed |
| Compound F | Pan PG antagonist | Form 1 | Form 1 | Became Backup of Compound E, New Record of Invention filed |
| Compound G | CsA analog | Amorphous | Amorphous | Confirmed by two separate Contract Research Organization (CRO) studies |
| Compound H | MKI | Amorphous | Form 1, 2, and 3 (F3 low energy form) | Provided seeds to Process Chem. for making crystalline materials |
| Compound I | Rosacea | Form 1 (dihydrate) | Form 2 (monohydrate) Greater stability to humidly at 25° C. | Form 2 recommended for manufacturing/development, results confirmed by CRO polymorph screen |
| Compound J | FPR2 | Form 1 | Form 2 (hydrate form) | Will impact Process Chemistry decision on delivering post-elevation form |
| Compound K | FPR2 | Form 1 | Form 2 and 3 | Became Backup of Compound J |
| Compound L | Glaucoma SR | Amorphous | Form 1 | Enabled the early-stage formulation |

Note:
The Pattern designation was made by a CRO working for Allergan; the forms designation were made by Allergan.

To date, comprehensive polymorph screening studies have been completed for Compound A, Bimatoprost (a commercial Allergan compound), Compound G, and Compound C. The following summarizes the comparison of our FRA results with those of the dedicated polymorph screening studies conducted at CROs.

For Compound A, nineteen crystalline forms were identified at the CRO. Our in house FRA only identified one solvate. However, this solvate was confirmed by the CRO study to become the low energy form upon desolvation. When this compound was studied by FRA, the workflow was in its initial stage, nevertheless, it proved rugged enough to find the precursor to the low energy form.

For bimatoprost, we were able to capture both forms which are the only two known crystalline forms so far.

For Compound G, a cyclosporine A (CsA) analog compound, no crystalline form was generated from FRA. Two comprehensive crystallization studies by leading CROs also failed to find a crystalline form.

For Compound C, the lead multiple kinase inhibitor (MKI) compound, the FRA process generated a number of crystalline forms starting with the amorphous API candidate. More importantly, we were able to identify the hydrate form, which was found to be the stable form during the formulation and solubility studies.

Comprehensive polymorph screening studies will be carried out for other Allergan compounds when they reach the appropriate development stages. Those results, once available, will be used for the additional refinement of the FRA workflow.

To summarize, the thermocycling method in the FRA workflow identified the low-energy forms within the design space defined by the model compounds. These results suggest that the thermocycling method usually not only produces crystalline forms but may expedite the formation of the most stable one by speeding up the kinetics of dissolution and nucleation process. If fact, temperature cycling has been widely used in hydrate screening and crystal engineering. In addition, most but not all of the metastable forms of the model compounds were found, the discovery of which can be used for candidate selection or designing further polymorph screening studies.

2.5 Additional Notes on Crystallization Experiments

Figure 5:
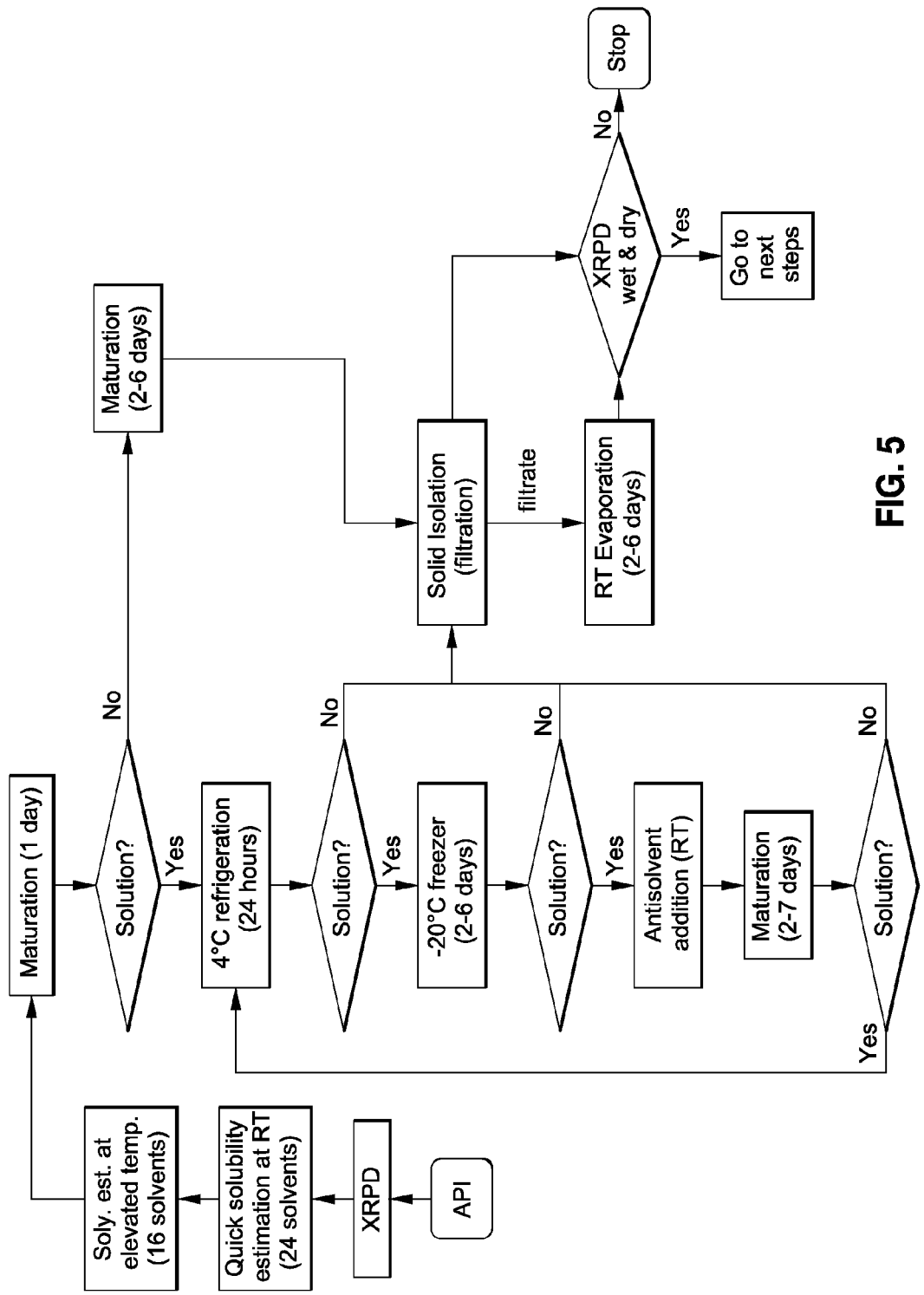
FIG. 5 shows the Typical FRA Experimental Workflow.

FIG. 5 shows a typical decision tree for conducting an FRA experiment. The candidate compound received from Discovery lab should be analyzed by XRPD to reveal its physical form. Then the solubilities of this compound in 24 solvents (Table 6 in Appendix I) are estimated based on visual inspection. Then 16 suspensions are prepared by the solvent systems selected from the initial estimations. These suspensions are inspected for cloudiness at 45° C. and then subjected to a rapid thermocycled slurrying experiments. If the samples remain cloudy afterwards, the slurrying experiments are continued for another three slow heat-cool-heat cycles. However, if clear solutions result from the fast thermocycling experiment, the samples will be cooled to 5° C. and further to −20° C. if necessary. Some antisolvent can be introduced to promote precipitation. Alternatively, evaporation can be used to generate solids if other crystallization methods are not successful. Solids generated at any point after any of the crystallization steps, should be analyzed by XRPD.

This section discusses our experimental experiences on conducting FRA.

2.5.1 Solvent Selection for the Crystallization Experiment

Figure 6:
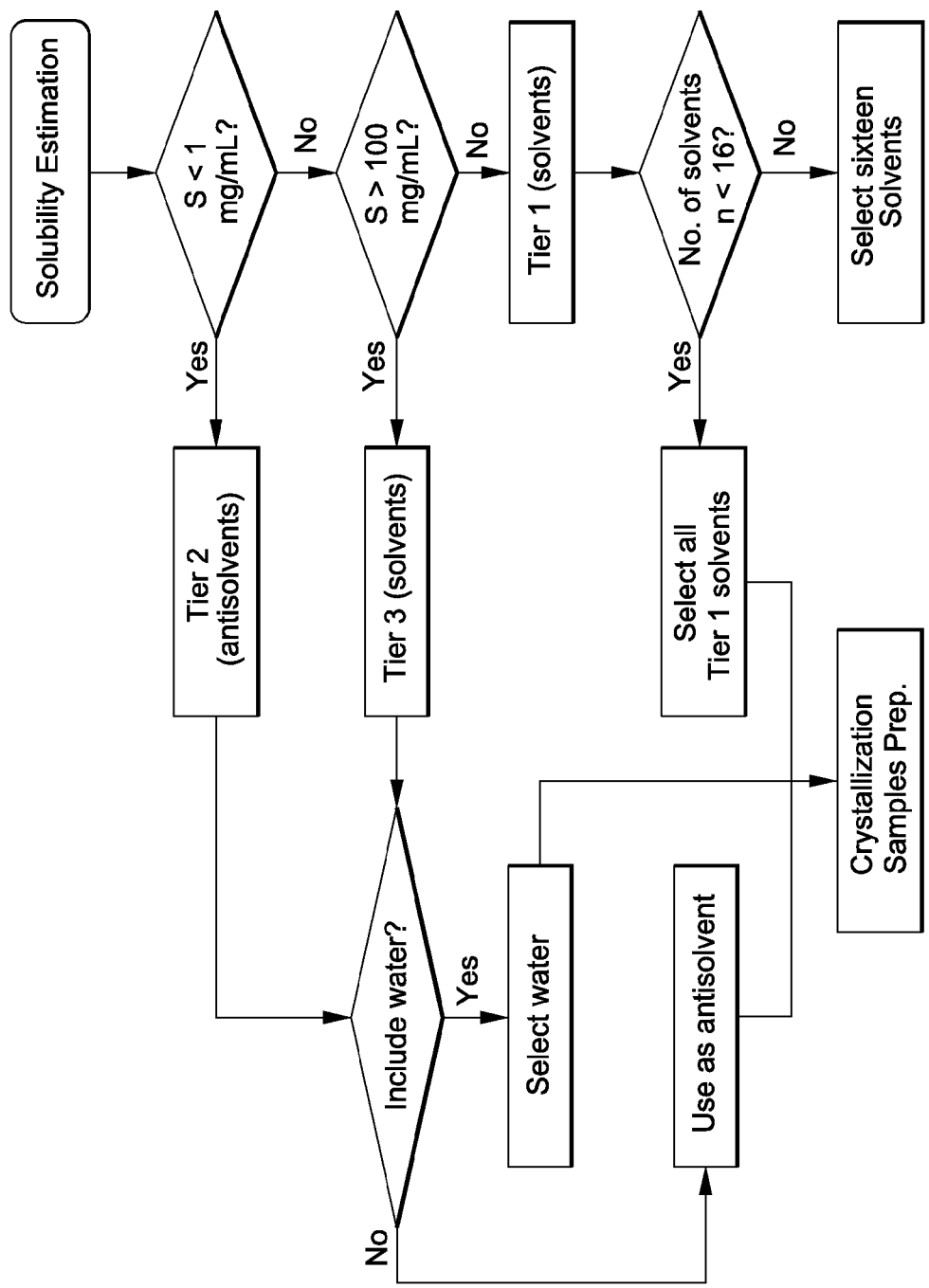
FIG. 6 shows the Decision Tree of Selecting the Solvents for FRA Experiments.

From the solubility (S) estimation, the initial twenty-four solvents are usually classified into three groups: (1) S<1 mg/mL, (2) S>100 mg/mL, and (3) S=1-100 mg/mL. Group (3) solvents are selected as the primary solvent for crystallization experiments. FIG. 6 presents a flowchart for selecting the solvents for FRA crystallization experiments. The following points summarize our experimental experience obtained during the verification stage of FRA:

- When both water and heptane are antisolvents and they have to be used to prepare solvent mixtures, ensure some of the experiments include one of the antisolvents and others include the other.
- When the solubility of the compound is too low in most of the solvents, start with the solvents showing best solubility and mix them with the top 16 solvents in the list.
- When the solubility of the compound is too high in most of the solvents, start with the solvent showing the poorest solubility and mix among them and try to include some of the top 16 solvents.

2.5.2. Crystallization of Amorphous Materials

Although amorphous materials have higher free energy levels than their crystalline or mesophase counterparts, they can often form mainly due to structural and kinetic reasons. In the former case, the molecular structure of the drug molecule does not allow favorable intra- or intermolecular interactions that can contribute to effective packing. In some extreme cases, the interaction is so weak that a very low-melting material such as oil may form. Prostaglandin compounds often fall within this category. In the latter case, the precipitation kinetics is too fast to allow crystallization. Because the crystallization conditions in the organic chemistry lab are rarely well controlled, amorphous materials are frequently generated. We have observed variability in crystallinity across different batches of the same discovery compound.

When the structure of a molecule is not readily amenable to crystallization, solvents may play important roles in facilitating the formation of ordered structures. For example, solvents may serve as linkers for the formation of crystalline structures. Previous experience with molecules of similar structures is very valuable. This includes observations by the medicinal chemists, manufacturing procedures reported by Process Chemistry, and relevant articles in the literature, etc.

Should the crystallization fail due to kinetic reasons, a properly controlled crystallization experiment can often be the solution. Observations during FRA experiments should be timely communicated to the medicinal chemists in order to maximize the synergy between the participants of the drug development process.

Finally, impurities should never be neglected because of their potentially significant roles, either positive or negative, during the crystallization process.[34-36] On the one hand, the impurity molecules may act as templates for the crystallization. On the other hand, the impurity molecules may also inhibit the crystal growth via interaction with the drug molecules. This issue is especially important for early-stage compounds. Sequential crystallization efforts are often very useful because the drug substance, if chemically stable, can be progressively purified.

As shown in Table 4, five amorphous compounds were studied by using the FRA workflow, four of them were crystallized. The only API that remained amorphous was Compound G, which resisted the best efforts by two expert CRO laboratories.

2.5.3. Hydrate

Due to the unique structure and properties of the water molecule, hydrate screening indeed should deserve a separate set of studies because hydrate formation may have a great impact on a drug substance in terms of solubility, dissolution rate, physical and chemical stabilities, and mechanical properties, etc.[37,38]

Although the design of the crystallization experiments provides the opportunities of hydrate formation by always choosing water as a solvent or antisolvent, the FRA is not specifically designed for hydrate screening. For that reason, when the as-received compound is a hydrate itself, the material can be directly subjected to FRA. For example, the FRA experiment of Compound I was conducted by using the form as received a dihydrate. After the FRA, a physically more stable hydrate was identified which was considered to be more suitable for development. Finally, if a crystalline anhydrous form is of greater interest, the material should be dehydrated before the FRA experiments, because the presence of water molecule may interfere with the crystallization process. In that sense, a solvate starting material should be treated similarly.

2.5.4. Oiling Out or Gelation

Oiling out and Gelation are two common phenomena observed during crystallization development in the pharmaceutical industry. Sonication by ultrasound energy can induce crystallization and control the precipitation process.[39,40] High energy sonication is able to induce crystallization of supersaturated solutions by providing a sufficient energy to reduce the metastable-zone width through an increased nucleation rate. However, caution should be exercised to avoid overheating because the agitation energy of sonication can also facilitate the dissolution of materials. Furthermore, chemical stability may also be at risk if an extended period of sonication is used. Our findings suggest that (1) adding excess volume of antisolvent before sonication treatment will help the precipitation out of a supersaturated solution; and (2) discrete sessions of sonication rather than continuous exposure can alleviate the stability concern.

Figure 7B:
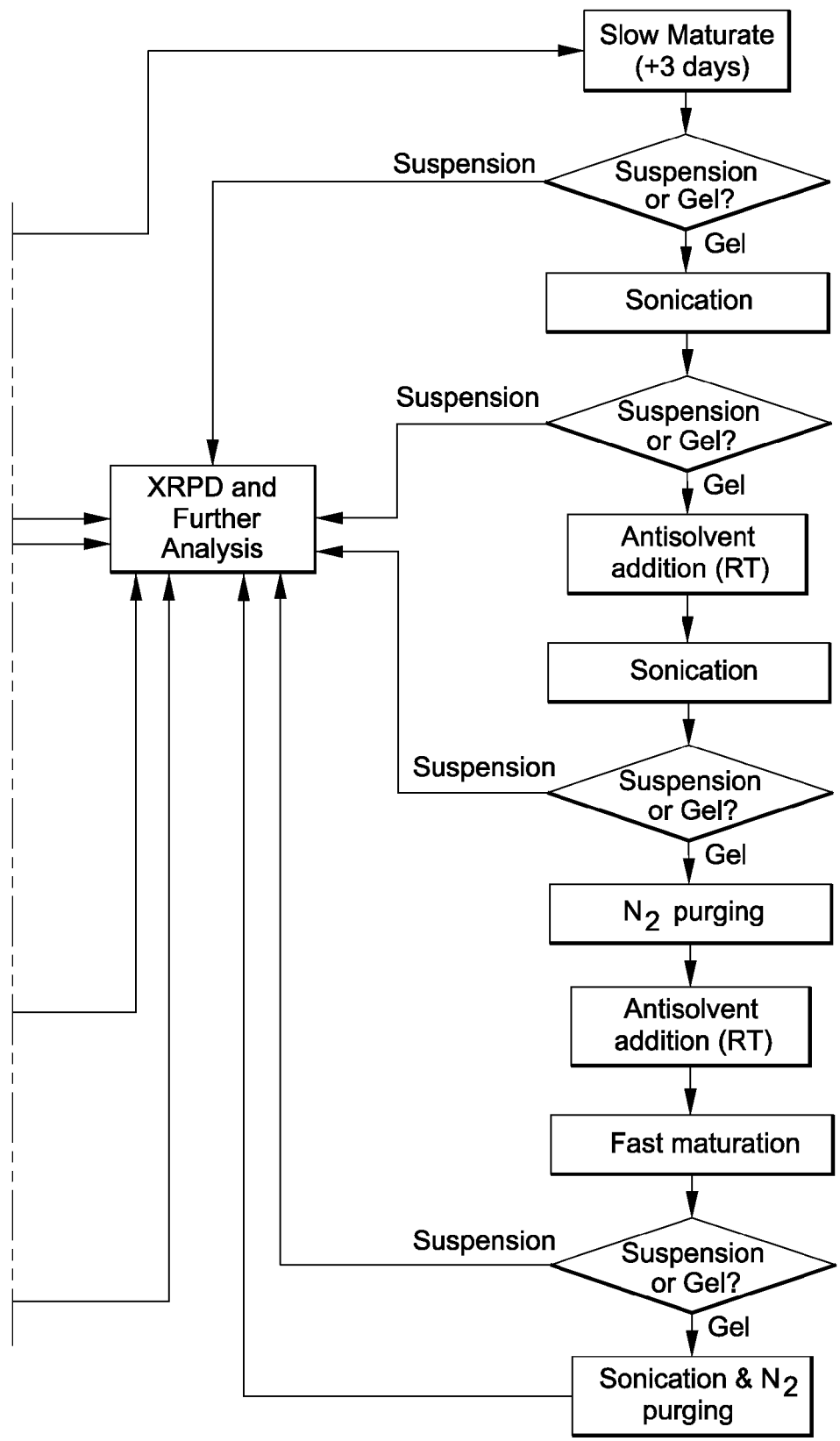

FIG. 7 shows the crystallization flowchart for Compound H. After the slow thermocycling, cooling, and antisolvent addition experiments, all the samples turned into yellow gels. By using sonication sessions, six out of sixteen samples were converted into solids among which three crystalline forms were generated. The form with the highest melting temperature was used as seed crystals with which larger quantities of the crystals were manufactured at a contract lab.

2.6 Post-FRA Characterization

Figure 8:
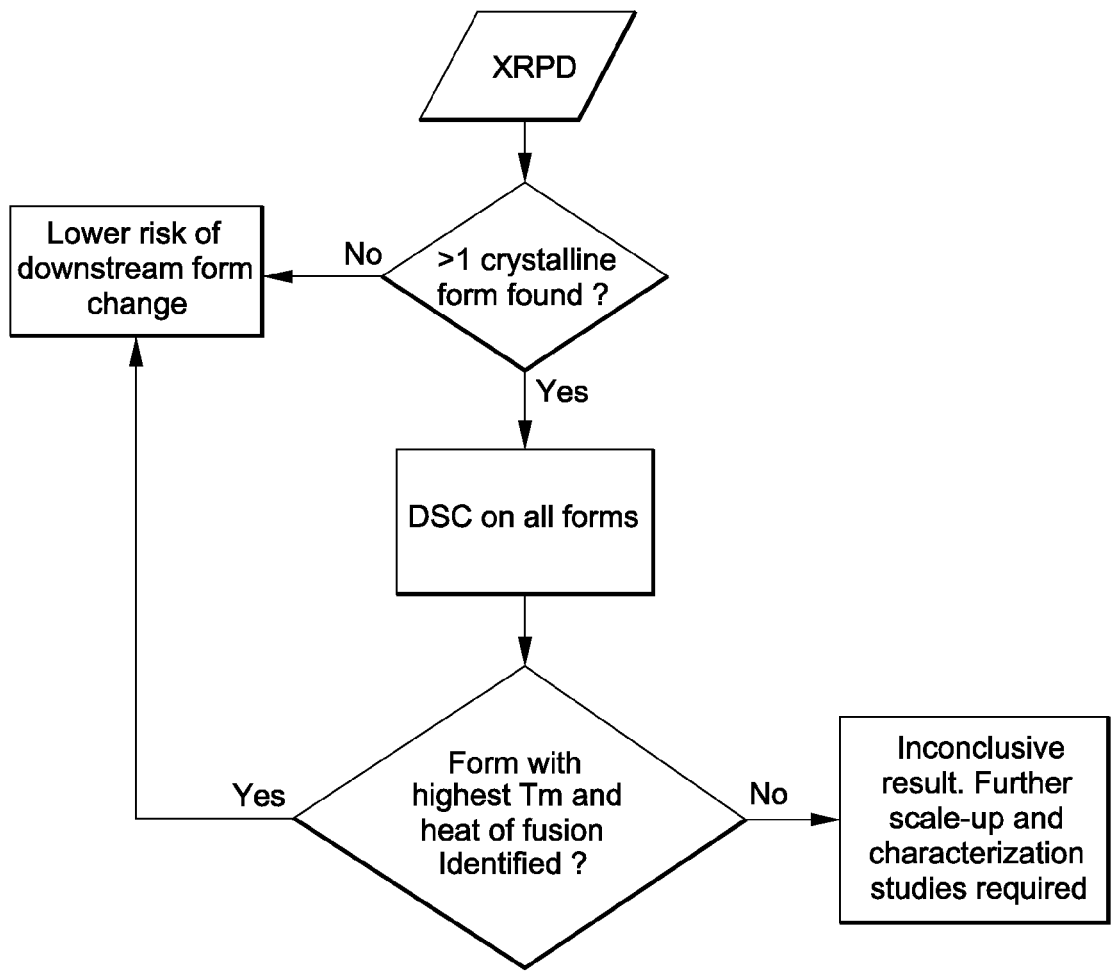
FIG. 8 shows the Schematic of Form Characterization Strategy for FRA.

FIG. 8 describes the strategy for the characterization of the products. XRPD is the primary tool for form identification for our FRA products. When the starting material is an amorphous material, the success of the FRA can be directly reflected by the XRPD results. Furthermore, commercial programs can be used to group the obtained patterns based on chemometric methods (such as principal component analysis, multivariate analysis, etc.) when multiple XRPD patterns are observed. In that case, a corresponding representative sample of each group should be further characterized by TGA and DSC to assess its polymorphic purity, detect signs of solvation (including hydration), and obtain the thermal properties of the forms. According to Burger's Heat-of-Fusion rule,[41] the one with the highest melting temperature and heat of fusion should be focused on the further studies. If enantiotropism is suspected, further form studies should be designed and conducted to locate the transition points.

2.7. Risks Associated with Crystallization Experiments

The primary limitations of the FRA workflow are limited experimental space covered and lack of metrics for decision making. In addition, some technical issues must be considered, such as the presence of impurities and the inherent chemical stability of the compound.

The presence of impurities can potentially impact the crystallization, either negatively or positively.[34] For example, some impurities can stop or retard crystal growth, while some others may enhance it. In addition, sometimes impurities selectively act on certain crystallographic faces so much as to change the crystal habit. In that sense, even the solvent from which the crystals are grown can be considered to be an impurity. Although some impurities need to be active at high concentrations, others will poison the crystallization when present in trace amounts. Discovery compounds are typically not sufficiently purified. As a result the potential impact of impurities should always be kept in mind.

The chemical stability of a compound under different crystallization conditions should never be neglected, especially when the stability information at the early stage is scarce. Experimental heat-cool-heat thermocycles during some crystallization experiments often stress the molecule. In addition, the incompatibility of the drug and solvent molecules is possible, for example, (trans-)esterification can happen with an alcohol molecule. Therefore, chemical identification of the final FRA products should be conducted for confirmation.

2.8. Strategic Triggers for FRA

Figure 9:
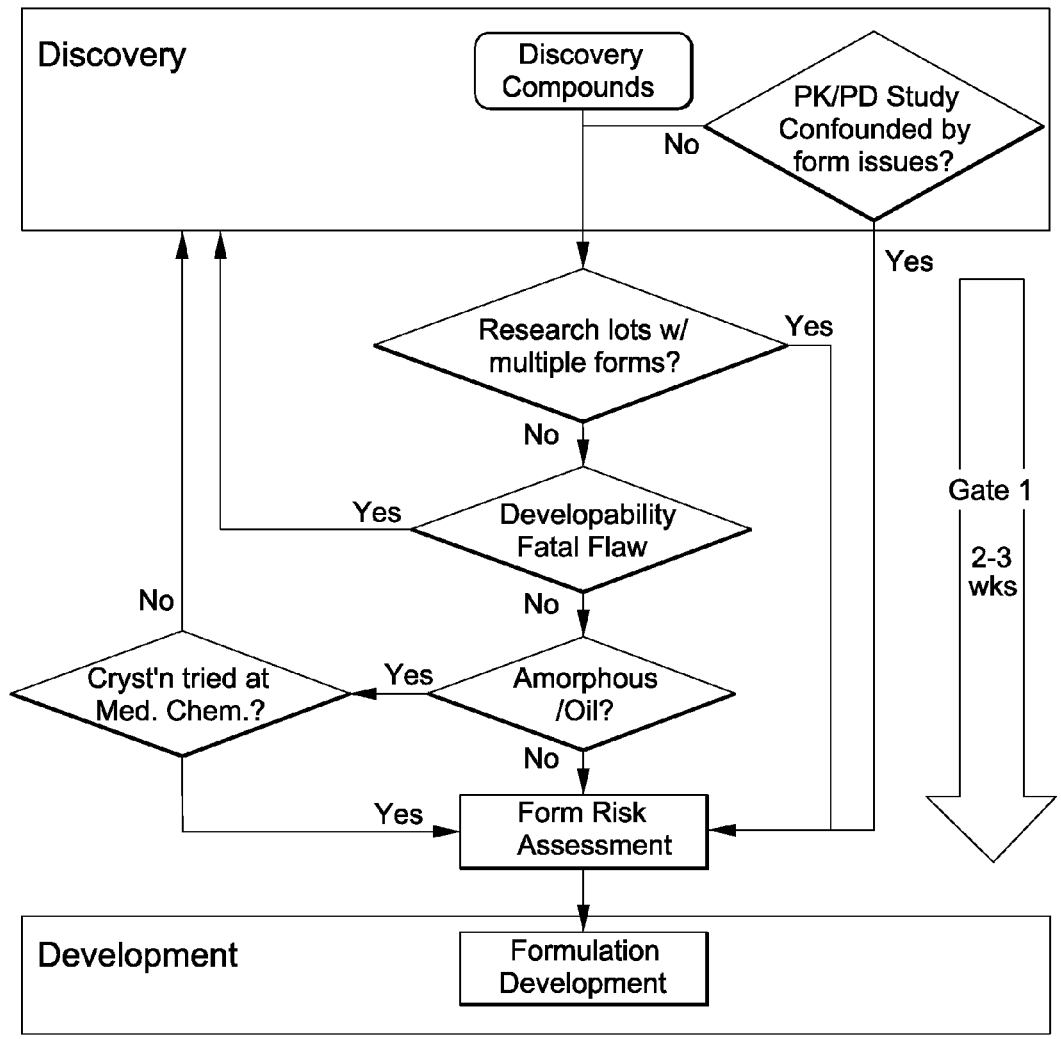
FIG. 9 shows the Strategic Flowchart of FRA.

Ideally, all compounds entering into early development should be evaluated for their polymorphic behaviors. However, because of the resource limitations associated with time and API availability, an appropriate strategy is required. FIG. 9 presents a strategic decision tree for conducting FRA.

The primary purpose of the FRA is to generate crystalline materials because the physical stability of an amorphous material often poses great challenges for reproducible formulation and bioavailability. In addition, when the raw material is oil, the difficulties in handling and processing may also be overwhelming. Medicinal chemists are encouraged to make some initial efforts to crystallize compounds because they usually have the most knowledge of the molecule in the early stage. An FRA experiment should be planned if the initial effort is not successful. In addition, an FRA should be considered when a compound is a solvate because of its possible toxicology or physical stability issues.

Another potential benefit of the FRA is some preliminary information of the polymorphism of a molecule. When multiple XRPD patterns are observed for various batches of the same compound, an FRA experiment is valuable for further understanding the polymorphic behavior of this molecule.

Usually, an FRA should be conducted after a candidate compound has met all the Gate 1 elevation criteria. However, the FRA should be performed to enable PK/PD studies when a non-developable form of a candidate drug substance is to be formulated.

Overall, the FRA workflow primarily focuses on converting an amorphous or oil compound into a crystalline solid to enable the Gate 1—ready molecule for downstream formulation activities, and the experimental scale and sequence are rationally designed to accommodate the API availability and the turnover time requirement before Gate 1. The risk of developing the amorphous form will be mitigated by using the initial crystalline form identified and recommended by the FRA. In addition, our experimental experiences have demonstrated that the FRA could probably capture the low energy forms of a molecule and it could sometimes preliminarily reveal its polymorphic propensity. These pieces of information could add additional value to the development process. However, a separate, dedicated polymorph screening should be designed and performed when the compound passes the Gate 1 assessment, but this activity is beyond the scope of the FRA strategy.

3. SUMMARY

A form risk assessment workflow was developed for the initial crystallization and preliminary evaluation of the polymorphic nature of new chemical entities by using <350 mg of API and a short timeframe (~2 weeks). The carefully designed thermal-cycling crystallization method appears to be efficient at crystallizing and producing the low-energy polymorphs for the compounds studied. The integration of different crystallization techniques, by using various solvent systems, enables the rapid identification of multiple solid forms with a success rate of approximately 80% of all the forms reported in the literature. Finally, knowledge and experience learned from the development of the FRA workflow can also be applied to help design the manufacturing process and define the storage conditions of drug substances. The results of the FRA may provide valuable information on the pharmaceutical developability of a potential molecule from discovery with minimum amounts of compounds.

4. REFERENCES

1. "Polymorphism in Pharmaceutical Solids", Drug and the Pharmaceutical Sciences, Vol. 95, Ed., H. G. Brittain.: Marcel Decker.
2. L.-F. Huang and W.-Q. Tong, "Impact of solid state properties on developability assessment of drug candidates", Advanced Drug Delivery Reviews, 56 (2004) 321-324.
3. C. R. Gardner, et al, "Drugs as Materials: Valuing Physical Form in Drug Discovery", Nature, 3 (2004) 926-934.
4. C. R. Gardner, "Drugs as materials: valuing physical form in drug discovery", Nature, 3 (2004) 926-934
5. S. Balbach and C. Korn, "Pharmaceutical evaluation of early development candidates 'the 100 mg-approach.'" International Journal of Pharmaceutics, 275 (2004) 1-12.
6. M. Pudipeddi and A. T. M. Serajuddin, "Trends in solubility of polymorphs", Journal of Pharmaceutical Sciences, 94 (2005) 929-939.
7. S. L. Price, "Computed crystal energy landscape for understanding and predicting organic crystal structures and polymorphism", Accounts of Chemical Research, 42 (2009) 117-126.
8. S. L. Price, "The computational prediction of pharmaceutical crystal structures and polymorphism", Advanced Drug Delivery Reviews, 56 (2004) 301-319.
9. S. R. Vippagunta, et al., "Crystalline Solids", Advanced Drug Delivery Reviews", 48 (2001) 3-26.
10. C. R. Gardner, et al., "Application of high throughput technologies to drug substance and drug product development", Computers and Chemical Engineering, 28 (2004) 943-953.
11. B. Rodriguez-Spong, et al., "General principles of pharmaceutical solid polymorphism: a supramolecular perspective', Advanced Drug Delivery Reviews, 56 (2004) 241-274.
12. C. Gu, et al. "Polymorph screening: influence of solvents on the rate of solvent-mediated polymorphic transformation", Journal of Pharmaceutical Sciences, 90 (2001) 1878-1890.
13. Y.-T. Sohn and K.-S. Kim, "Study on Polymorphism of Cimetidine", J. Kor. Pharm. Sci., 23 (1993) 81-87.
14. W. I. Cross, et al., "A Whole Output Strategy for Polymorph Screening: Combining Crystal Structure Prediction, Graph Set Analysis, and Targeted Crystallization Experiments in the Case of Diflunisal", Crystal Growth & Design, 3 (2003) 151-158.
15. M. A. Hassan, et al., "Characterization of famotidine polymorphic forms, International Journal of Pharmaceutics", 149 (1997) 227-232.

16. B. Nicolaï, et al., "Polymorphism and solvation of indomethacin", J. Therm Anal calorim, 102 (2010) 211-216.
17. F. Vrečer, et al., "Characterization of Piroxicam crystal modifications", International Journal of Pharmaceutics", 256 (2003) 3-15.
18. K. Sato, "Stability, Occurrence and Step Morphology of Polymorphs and Polytypes of Stearic Acid: I. Stability and Occurrence", Journal of Crystal Growth, 87 (1988) 236-242.
19. M. Lagas and C. F. Lerk, "The Polymorphism of Sulphathiazole", International Journal of Pharmaceutics", 8 (1981) 11-24.
20. M. Allersø, et al, "Solvent Diversity in Polymorph Screening", Journal of Pharmaceutical Sciences", 97 (2008) 2145-2159.
21. C. Gu, et al. "Grouping solvents by statistical analysis of solvent property parameters: implication to polymorph screening", International Journal of Pharmaceutics, 283 (2004) 117-125.
22. Allesø, et al, "Solvent subset selection for polymorph screening", Chemometrics, 22 (2008) 621-631.
23. J. M. Miller, "Identifying the stable polymorph early in the drug discovery-development process, Pharmaceutical Development and Technology, 10 (2005) 291-297.
24. J. Aaltonen, et al. "Solid form screening—a review", European Journal of Pharmaceutics and Biopharmaceutics, 71 (2009) 23-37.
25. Crystallization, $4^{th}$ ed., J. W. Mullin, Elsevier Butterworth-Heinemann.
26. R. Boistelle; J. P. Astier, Journal of Crystal Growth 90 (1988) 14-30.
27. M. R. Abu Bakar, et al, "Seeded batch cooling crystallization with temperature cycling for the control of size uniformity and polymorphic purity of sulfathiazole crystals", 13 (2009) 1343-1356.
28. T. Threlfall. "Crystallization of polymorphs: thermodynamic insight into the role of solvent", Org. Process Res. Dev., 4 (2000): 384-390.
29. A. Getsoian, et al., "One-solvent polymorph screen of carbamazepine", International Journal of Pharmaceutics, 348 (2008) 3-9.
30. S. R. Byrn, et al., Chemical Materials, 6 (1994) 1148.
31. P. H. Stahl, "Towards better safety of drugs and pharmaceutical products", Braimer, D. D., Ed., Elsevier/North Holland Biomedical Press: Amsterdam, 1980.
32. Ostwald, W. Lehrbuch der Algemeinen Chemie, 2, Englemann, Leipzig, (1896) 444.
33. Ostwald, W. Studien Ober die Bildung and Umwandlung fester Korper. Zeitschrift für Physikalische Chemie, 22 (1897) 289-330.
34. Y. Gong, et al., "Stable-Form Screening: Overcoming Trace Impurities that Inhibit Solution-Mediated Phase Transformation to the Stable Polymorph of Sulfamerazine", Journal of Pharmaceutical Sciences, 97 (2008) 2130-2144.
35. C.-H. Gu, et al, "Stabilization of a metastable polymorph of sulfamerazine by structurally related additives", Journal of Crystal Growth, 235 (2002) 471-481.
36. M. B. Hursthouse, et al, "Why do organic compounds crystallize well or badly or ever so slowly? Why is crystallization nevertheless such a good purification technique?", Organic Process Research & Development, 13 (2009) 1231-1249.
37. F. Tian, et al, "Factors affecting crystallization of hydrates", Journal of Pharmacy and Pharmacology, 62 (2010) 1534-1546.
38. R. K. Khankari and D. J. W. Grant, "Pharmaceutical Hydrate", Thermochimica Acta, 248 (1995) 61-79.
39. A. Kordylla, et al., "Modeling ultrasound-induced nucleation during cooling crystallization", Chemical Engineering Science, 64 (2009) 1635-1642.
40. H. Li, et al., "The application of power ultrasound to reaction crystallization", 13 (2006) 359-363.
41. A. Burger and R. Ramberger, "On the Polymorphism of Pharmaceuticals and Other Molecular Crystal. II", Mikrochimica Acta, 2 (1979) 273-316.

APPENDIX

I. Amount of Materials Required for Characterization

| Experiment | Amount required per experiment (mg) |
|---|---|
| Form Screening | |
| Solubility estimation | 1.5 mg |
| polymorphism | 15-20 mg |
| Physicochemical Properties | |
| X-ray diffraction | 5 mg (reusable) |
| TGA | 3 mg |
| DSC | 3 mg |
| Raman | 1-2 mg |
| FT-IR | 2-3 mg (reusable) |
| hygroscopicity (for hydrate) | 3 mg |
| microscopy | Optical: 2 mg (reusable if dry) SEM: 1 mg |
| NMR | 10-20 mg |

II. Characterization of the FRA Products

The following sections describe the typical methods for the characterization of the products generated from FRA. These techniques, individually, are selected to study certain molecular level or macroscopic-level physical properties of a material. The information acquired by using the combination of these tools provides a profile of the pharmaceutical solid of interest.

X-Ray Powder Diffraction

The X-ray power diffraction (XRPD) technique is the predominant tool for the routine characterization of polymorphs and pseudomorphs. The profile of an XRPD pattern of a sample can be used to define its physical form. For example, a halo without apparent peaks in a XRPD pattern indicates that this material is non-crystalline and most likely amorphous. Calibrate the Rigaku Miniflex X-ray diffractometer with a standard. The system can scan six samples consecutively. A peak at 2θ of 28.44° C. validates the equipment. About 2-3 mg sample is needed for each scan. A recommended scan condition will be a range between 3 and 45° (2θ) and a step size of 0.05° (2θ) at 2° (2θ) per minute. A narrows scan range may be used whenever applicable on the condition that the patterns are differentiable within that range.

Thermal Gravimetrical Analysis

A TGA Q2000 (TA instruments) system calibrated thermomagnetically is used for measuring solvent/moisture content of samples and evaluating thermal stability of the same. About 1.5-2.5 mg sample is needed for each test. Run a TGA for each of the sample at 10° C. per minute from R.T. to 300° C. The nitrogen purge rate of 20 mL/min. Percent weight loss from R.T. to 120° C. is used to determine type of sample pan in DSC measurement and to help explanation of DSC profiles. Decomposition temperature is used to design DSC scan range.

Differential Scanning Calorimetric Analysis

Differential scanning calorimetry (DSC) is one of the most important techniques for understanding the thermal stability, polymorphism, hydration and solvation states. Calibrate the TA DSC Q5000 equipment using an Indium standard. If percent weight loss from 25-120° C. by TGA curve is less than 0.5%, nonhermetic T-zero pans are used for containing the samples. Otherwise, hermetic pans will be used instead. The nitrogen purge rate is 50 mL/min.

Load ca. 2-3 mg sample into sample pan. Run a standard DSC for each of the sample at 10° C. per min. Maintain the nitrogen purge rate at 50 mL/min. Combine TGA and MDSC data to verify dehydration and decomposition temperatures, and assign endothermic and/exothermic peaks glass transition and melting from reversing heat flow (or reversing heat capacity if necessary) signal in MDSC thermographs. Hot Stage Microscopy may be employed in complicated situations where multiple thermal events are overlapped and cannot be explained by TGA/MDSC data.

Fourier Transform Infrared Spectroscopy

A Thermo Nicolet 6700 FTIR system with a Duroscope® ATR module is used for collecting IR spectra. The peak position and intensity can be used for phase identification such as differentiation of solid forms, confirmation of forming a salt, and detection of solvents in solvates or as residues, etc. Calibrate the Thermo Electron FTIR equipment by comparing the background spectra with the IR reference background of the standard diamond. Press the sample against the window to ensure the entire diamond window is covered with sample. A typical scan range is 600-4000 cm-1 and resolution is 4 cm-1. A scan number of 32 will be applied on both background and all samples.

Nuclear Magnetic Resonance (NMR)

NMR analysis is essential to confirm the chemical identity of a material generated from FRA. Apply this technique whenever it is necessary. Select representative FRA samples and send to Process Chemistry Department for NMR assays.

Polarized Light Microscopy

This technique features minimal sample preparation, little usage of material, directly observable information. It is a great supplementary tool for other techniques such as DSC, PSD, and HSM, etc. A PAXCam polarized light microscope (OLYMPUS BX51) is used for acquiring optical images and examining birefringence. Objectives of 40-500× may be selected as appropriate. Apply sample onto glass slide and cover with cover slide, then observe under microscope with polarized plug-in filter. Appearance of birefringence is indicative of crystalline material. However, absence of birefringence doesn't exclude the possibility of crystals.

Capillary Melting Experiments

This experiment is optional for crystalline forms generated during the scale-up experiments. The decomposition temperature of each sample will be estimated. In addition, other thermal events such as melting can also be estimated by recording the temperatures of the initial appearance of liquid and the disappearance of all solid. Conduct capillary melting experiments on the sample using a Buchi B545 melting point apparatus. Tap the open end of capillary onto a small pile of powder sample (grind if necessary to ensure smooth loading) and turn the capillary open end up, and tap the closed end onto a hard surface. The solid should be tightly packed to a depth of 2-3 mm. Decomposition temperature of each sample will be estimated by heating the sample from R.T. to 300° C. at 10-20° C./min.

III. Temperature Programs of Thermocycling Experiments

Figure 10:
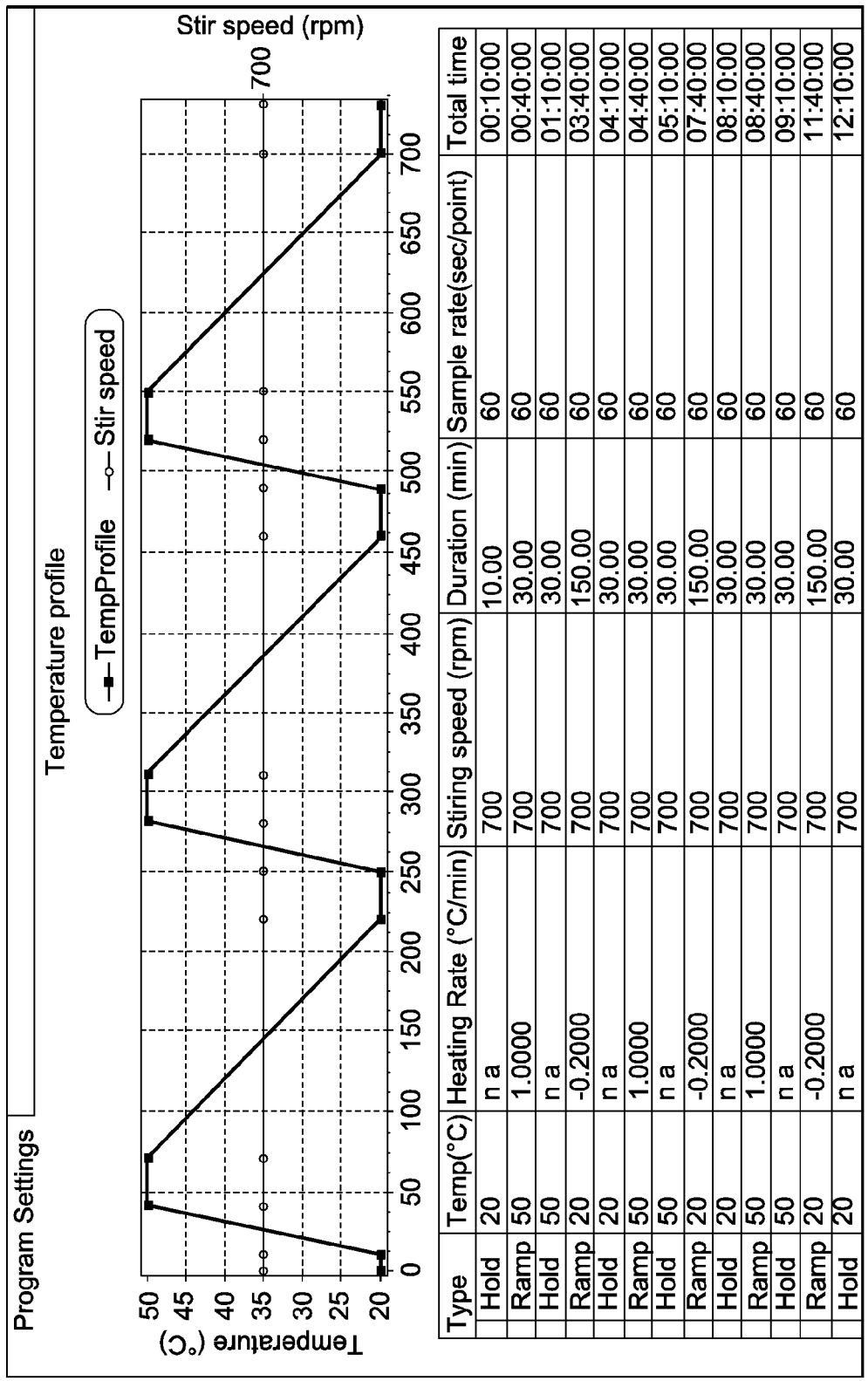
FIG. 10 shows the Temperature Profile of the Initial Thermocycling Experiment.
Figure 11:
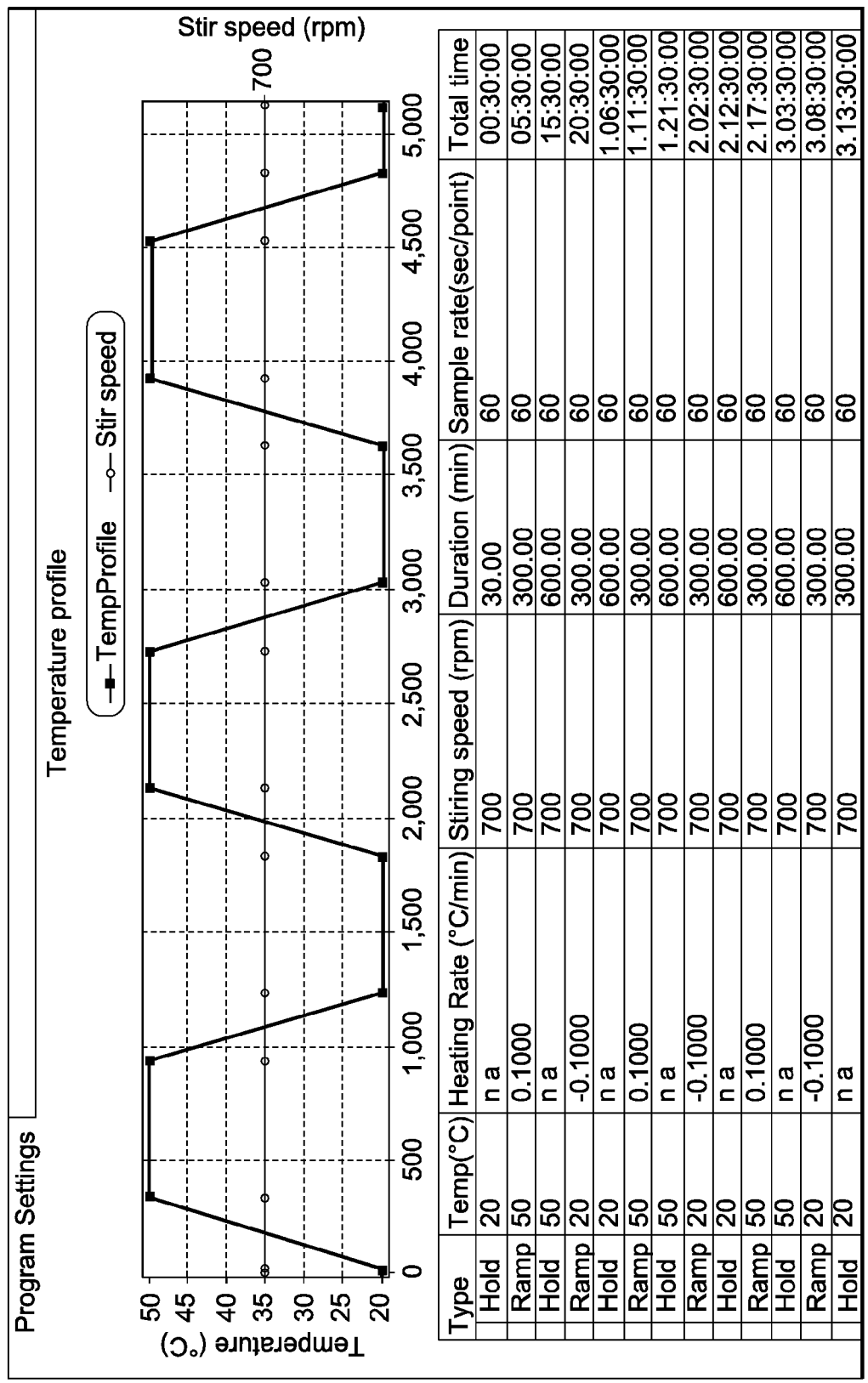
FIG. 11 shows the Temperature Profile of the Slow Thermocycling Experiment.

If the calculated solubility is less than 100 mg/mL in the solubility estimation test, prepare slurry of the compound in 0.25-1.75 mL solvent by adding excess amount of solid (20±3 mg). Conduct the following thermo-cycling experiment (FIG. 10): Briefly, a thermocycling experiment should be configured to control the temperature cycles between 20 and 50° C. with the heating rate of 1° C./min. and cooling rate of 0.2° C./min. A minimum of three heat-cool-heat cycles is recommended. At the end of each heating or cooling step, the samples should be isothermal for at least 30 minutes to allow temperature equilibrium (at both 20 and 50° C.) or allow crystal growth (at 20° C.). In addition, the samples should be magnetically stirred at 700 rpm. After the initial maturation, visually inspect each sample for clear solution or gel formation. If suspension remains, proceed with a slow maturation as shown in FIG. 11. Both the heating and cooling rate are typically 0.1° C./min. which is the slowest the rate that the equipments can control. The equilibrium time or crystal growth time should be at least 300 minutes after each heating or cooling step. The total time of a slow maturation experiment for three-cycle temperature program is typically three to four days.

IV. Solubility Estimation at Ambient Temperatures

TABLE 5

Properties of the Solvents Used for Form Risk Assessment

| Solvent | Solvent ID | Dielectric constant | dipole moment | Solubility parameter | MW | Density (g/mL) | b.p. (° C.) |
|---|---|---|---|---|---|---|---|
| Heptane | Hep | 1.9 | 0 | 14.1 | 100.2 | 0.684 | 98 |
| 1,4-dioxane | Diox | 2.2 | 0 | 19.3 | 88.1 | 1.034 | 101 |
| Toluene | Tol | 2.4 | 0.36 | 17.0 | 92.1 | 0.865 | 110.6 |
| Cumene | Cum | 2.4 | 0.65 | 16.0 | 120.2 | 0.862 | 152.4 |
| Anisole | Ani | 4.3 | 1.38 | 18.3 | 108.1 | 0.995 | 154 |
| Diethyl ether | Ether | 4.3 | 1.15 | 15.2 | 74.1 | 0.715 | 34.6 |
| Isopropyl acetate | iPrOAc | 6.0 | 1.79 | 17.1 | 102.1 | 0.87 | 89 |
| Ethyl acetate | EtOAc | 6.0 | 1.78 | 17.3 | 88.1 | 0.902 | 77 |
| Tetrahydrofuran | THF | 7.6 | 1.63 | 18.4 | 72.1 | 0.889 | 66 |
| Dichloromethane | DCM | 9.1 | 1.6 | 20.0 | 84.9 | 1.325 | 40 |
| methyl isobutyl ketone | MIBK | 13.1 | 4.2 | 17.8 | 100 | 0.8 | 117 |
| 1-Butanol | BuOH | 17.8 | 1.66 | 21.1 | 0.88 | 0.81 | 118 |
| Methyl ethyl ketone | MEK | 18.5 | 2.76 | 17.9 | 72.1 | 0.8 | 79.6 |
| Isopropyl alcohol | IPA | 20.1 | 1.68 | 22.1 | 60.1 | 0.804 | 97 |
| Acetone | Ace | 20.7 | 2.88 | 19.0 | 58.1 | 0.791 | 56 |

TABLE 5-continued

Properties of the Solvents Used for Form Risk Assessment

| Solvent | Solvent ID | Dielectric constant | dipole moment | Solubility parameter | MW | Density (g/mL) | b.p. (° C.) |
|---|---|---|---|---|---|---|---|
| Ethanol | EtOH | 24.3 | 1.69 | 24.9 | 46.1 | 0.816 | 78 |
| N-Methyl-2-pyrrolidine | NMP | 32.2 | 4.1 | 23.0 | 99.1 | 1.03 | 204.3 |
| Methanol | MeOH | 32.6 | 1.7 | 28.4 | 32.0 | 0.791 | 64.7 |
| Ethylene glycol | EG | 37.0 | 2.28 | 29.3 | 62.1 | 1.11 | 197.3 |
| Acetonitrile | ACN | 37.5 | 3.92 | 22.9 | 41.0 | 0.786 | 81 |
| N,N-Dimethylformamide | DMF | 38.3 | 3.82 | 21.5 | 73.1 | 0.944 | 153 |
| Nitromethane | NitroMe | 39.4 | 3.46 | 24.2 | 61.0 | 1.127 | 101 |
| Dimethyl sulfoxide | DMSO | 46.5 | 3.96 | 23.9 | 78.1 | 1.101 | 189 |
| Water | H2O | 80.4 | 1.85 | 45.8 | 18.0 | 1 | 100 |

All references cited herein are hereby incorporated by reference in their entirety.

The foregoing descriptions details specific methods that can be employed to practice the present invention, and represents the best mode contemplated. It should not be construed as limiting the overall scope hereof; rather, the ambit of the present invention is to be governed only by the lawful construction of the appended claims.

What is claimed is:

1. A process for the rapid identification and preparation of a crystalline form of an organic compound by using sub-gram level of said organic compound, said process comprising the steps of:

(a) Conducting an initial x-ray powder diffraction (XRPD) analysis of a starting sample of said organic compound; thereafter (b) Conducting an initial visual solubility estimation of the organic compound in each of several solvents or a mixture of solvents thereof at ambient or room temperature; thereafter (c) Conducting a solubility estimation of the organic compound in each of a subset of the several solvents of step (b) or a mixture of said solvents at elevated temperature by subjecting a suspension or emulsion of the organic compound in said solvent or solvent mixture to temperature-cycled slurrying for a fixed period of time; and thereafter performing any one of: i) steps (d1) through (d5), (e1), (e2) and (f4); ii) steps (f1) through (f4); iii) steps (d1), (e1), (e2) and (f4); iv) steps (d1), (d2), (e1), (e2) and (f4); and (v) steps (d1) through (d4), (e1), (e2) and (f4) set forth below:

(d1) If the sample of the organic compound and solvent/solvent mixture from step (c) remains a clear solution, then cooling the solution of said organic compound in said solvent or solvent mixture to a temperature of about 3° C. to about 6° C. and maintaining said solution at said temperature for a fixed period of time to induce super saturation;

(d2) If the sample of the organic compound and the solvent/solvent mixture is still a clear solution at the end of said fixed period of time in step (d1), then further cooling said solution to a temperature of about −18 to about −22° C. for a fixed period of time that is longer than the period of time set forth in step (d1) above;

(d3) If the sample of the organic compound and the solvent/solvent mixture is still a clear solution at the end of said fixed period of time in step (d2), then adding an antisolvent/antisolvent mixture at room temperature to create a suspension or emulsion of the organic compound in said mixture of solvent and antisolvent;

(d4) Further subjecting said suspension or emulsion of the organic compound in said mixture of solvent and antisolvent from step (d3) to temperature-cycled slurrying for a period of time longer than that set forth in step (d1);

(d5) If the sample of the organic compound and the mixture of solvent and antisolvent at the end of step (d4) is a clear solution, then further performing steps (d1) through (d4) once more as long as the sample of the organic compound and the solvent/solvent mixture in steps (d1) and (d2) is still a clear solution;

(e1) If the sample of the organic compound and the solvent/solvent mixture at the end of any of steps (d1) or (d2) are not clear solutions, or the sample of the organic compound and the mixture of solvent and antisolvent at the end of step (d4) is not a clear solution, then performing a filtration to isolate a "dry" sample of said organic compound from the solvent/solvent mixture or solvent/antisolvent mixture;

(e2) evaporating the solvent/solvent mixture or the solvent/antisolvent mixture from step (e1) in a slow, diffusion controlled process for a fixed period of time that is at least 24 hours long to isolate the residue, which is a "wet" sample of the organic compound;

(f1) further subjecting the sample of the organic compound and the solvent/solvent mixture to temperature-cycled slurrying for a period of time longer than that in step (c) if said sample of the organic compound and the solvent/solvent mixture is not a clear solution;

(f2) performing a filtration to isolate a "dry" sample said organic compound from the solvent/solvent mixture in step (f1);

(f3) evaporating the solvent/solvent mixture from step (f2) in a slow diffusion controlled process for a fixed period of time that is at least 24 hours long to isolate the residue which is a "wet" sample of the organic compound;

(f4) conducting an XRPD analysis of wet and dry samples of said organic compound from any of step (e1), (e2), (f2) and (f3) and compare said analysis with the analysis carried out in step (a);

wherein significant differences in the XRPD spectra between the sample in step (a) and the sample in any one of steps (e1), (e2), (f2) and (f3) likely indicate the presence of a new crystalline form of said organic compound.

2. The process of claim 1, wherein the organic compound is an active pharmaceutical ingredient (API).

3. The process of claim 1, wherein the sub-gram level of said organic compound is an amount that is less than 350 mg.

4. The process of claim 1, wherein step (b) comprises estimating the solubilities of the organic compound in at least 20 different solvents.

5. The process of claim 1, wherein the starting sample in step (a) is an amorphous or crystalline material.

6. The process of claim 1, wherein in step (c), said temperature-cycled slurrying is conducted with a single solvent, and wherein the concentration of said suspension or emulsion of the organic compound in the single solvent at ambient or room temperature is 5-10 times lower than the concentration at elevated temperature.

7. The process of claim 1, wherein in step (c), the fixed period of time is about 20 to about 26 hours.

8. The process of claim 1, wherein in step (c), the temperature-cycled slurrying involves at least three heat-cool-heat temperature cycles.

9. The process of claim 1, wherein in step (d1), wherein said cooling is carried out at a cooling rate of about 0.1° C. per minute.

10. The process of claim 1, wherein in step (d1), wherein said fixed period of time is about 22 to about 26 hours.

11. The process of claim 1, wherein in step (d2), the fixed period of time is about 2 to about 6 days.

12. The process of claim 1, wherein in step (d4), the fixed period of time is about 2 to about 7 days.

13. The process of claim 1, wherein in steps (e2) and (e3), the fixed period of time is about 2 to about 6 days.

14. The process of claim 1, wherein the crystalline form is the most thermodynamically stable crystalline form.

15. The process of claim 1, wherein said process has the advantage in being completed in a period of about 2 to about 3 weeks.

16. The process of claim 2, wherein said process has the advantage of facilitating decision-making on the developability of a drug candidate.

17. The process of claim 2, wherein said process has the advantage in enabling an organic compound drug candidate to be elevated to early development.

* * * * *